United States Patent
Austyn et al.

(10) Patent No.: US 9,402,897 B2
(45) Date of Patent: Aug. 2, 2016

(54) IMMUNE MODULATION WITH LONG RANGE ORDERED, LAYERED DOUBLE HYDROXIDES

(75) Inventors: Jonathan M. Austyn, Oxford (GB); Dermot M. O'Hare, Oxford (GB); Bart Lambrecht, Ghent (BE)

(73) Assignees: ISIS INNOVATION LTD., Oxford (GB); UNIVERSITEIT GENT, Ghent (BE)

( * ) Notice: Subject to any disclaimer, the term of this patent is extended or adjusted under 35 U.S.C. 154(b) by 0 days.

(21) Appl. No.: 13/640,213

(22) PCT Filed: Apr. 11, 2011

(86) PCT No.: PCT/GB2011/050715
§ 371 (c)(1),
(2), (4) Date: Nov. 19, 2012

(87) PCT Pub. No.: WO2011/124931
PCT Pub. Date: Oct. 13, 2011

(65) Prior Publication Data
US 2013/0064795 A1    Mar. 14, 2013

(30) Foreign Application Priority Data
Apr. 9, 2010  (GB) ................... 10005931.9

(51) Int. Cl.
| | |
|---|---|
| A61K 39/39 | (2006.01) |
| C01F 7/00 | (2006.01) |
| B82Y 30/00 | (2011.01) |
| C01G 1/02 | (2006.01) |
| A61K 39/00 | (2006.01) |

(52) U.S. Cl.
CPC ............. *A61K 39/39* (2013.01); *B82Y 30/00* (2013.01); *C01F 7/005* (2013.01); *C01G 1/02* (2013.01); *A61K 2039/55505* (2013.01); *C01P 2002/22* (2013.01); *C01P 2002/50* (2013.01); *C01P 2002/78* (2013.01); *C01P 2004/52* (2013.01); *C01P 2004/62* (2013.01); *C01P 2004/64* (2013.01); *C01P 2006/80* (2013.01); *C01P 2006/90* (2013.01)

(58) Field of Classification Search
None
See application file for complete search history.

(56) References Cited

FOREIGN PATENT DOCUMENTS

| EP | 0 987 328 A2 | 3/2000 |
|---|---|---|
| KR | 2009055948 | 6/2009 |
| WO | 03/000284 A1 | 1/2003 |
| WO | WO 03/000284 * | 1/2003 |
| WO | 2006/085079 A2 | 8/2006 |
| WO | 2006/091009 A1 | 8/2006 |

OTHER PUBLICATIONS

Constantino VRI et al. (1995). Basic Properties of Mg2+(1-x)Al3+(x) layered double hydroxides intercalated by carbonate, hydroxide, chloride, and sulfate anions. Inorganic Chemistry, v34, p883-892.*
"Inorganic Acids." (2005). Retreived from http://chemweb.unp.ac.za/chemistry/Physical_Data/pKa_values.htm.*
Wayback Machine snapshot of "Inorganic Acids", establishing a publication date of Ref V of 2005.*
Lou Y et al. (2004). Dendritic cells strongly boost the antitumor activity of adoptively transferred T cells in vivo. Cancer Research, v64, p6783-6790.*
Xu ZP et al. (2006). Stable suspension of layered double hydroxide nanoparticles in aqueous solution. JACS, v128, p. 36-37.*
Xu ZP et al. (2008). Subcellular compartment targeting of layered double hydroxide nanoparticles. Journal of Controlled Release, v130, p. 86-94.*
Choy JH et al. (2000). Inorganic layered double hydroxides as nonviral vectors. Angew Chem Int Ed, v39(22), p. 4041-4045.*
Choy JH et al. (2001). Cellular uptake behavior of [gamma-32P] labeled ATP-LDH nanohybrids. Journal of Materials Chemistry, v11, p. 1671-1674.*
Cantrell et al. (2005). Structure-reactivity correlations in MgAl hydrotalcite catalysts for biodiesel synthesis. Applied Catalysis A: General, v285, p. 183-190.*
Xu et al. (epub Apr. 1, 2010). Synthesis of Mg-Al-carbonate layered double hydroxide by an atom-economic reaction. Particulogy, v8, p. 198-201, plus screen capture for epub date.*
Khan, Aamir I., et al., Intercalation chemistry of layered double hydroxides: recent developments and applications, J. Mater. Chem.,12 (2002) 3191-3198.
Li, Ang, et al., Signalling pathways involved in the activation of dendritic cells by layered double hydroxide nanoparticles, Biomaterials, 31 (2010) 748-756.
Li, Ang, et al., The use of layered double hydroxides as DNA vaccine delivery vector for enhancement of anti melanoma immune response, Biomaterials, 32 (2011) 469-477.
GB Intellectual Property Office, GB Patent Search Report for Patent Application No. GB1005931.9 dated Aug. 13, 2010, 3 pgs.

(Continued)

*Primary Examiner* — Scott Long
*Assistant Examiner* — Sean C Barron
(74) *Attorney, Agent, or Firm* — Christopher J. Knors; Moore & Van Allen PLLC

(57) ABSTRACT

The invention provides a long range ordered, layered double hydroxide compound for use in modulating an immune response to an antigen, and an immune modulator composition comprising the layered double hydroxide and an interlayer anion A. The compound is $[M^{II}_{(1-x)}M^{III}_x(OH)_2]^{x+}[A^{n-}_{x/n}]$, in which $M^{II}$ is a divalent metal cation or a mixture of two or more divalent metal cations, $M^{III}$ is a trivalent metal cation or a mixture of two or more trivalent meta cations, or a mixture of one or more trivalent metal cation with one or more quadravalent metal cation, x is from 2:1 to 1:4, and A is an interlayer anion having a charge n, wherein optionally some or all of the interlayer anion A may be replaced by one or biologically active agent and/or one or more antigen, and wherein A is selected from conjugate bases of acids having a pKa of −4 or higher.

9 Claims, 18 Drawing Sheets

(56) References Cited

OTHER PUBLICATIONS

Figure 1:
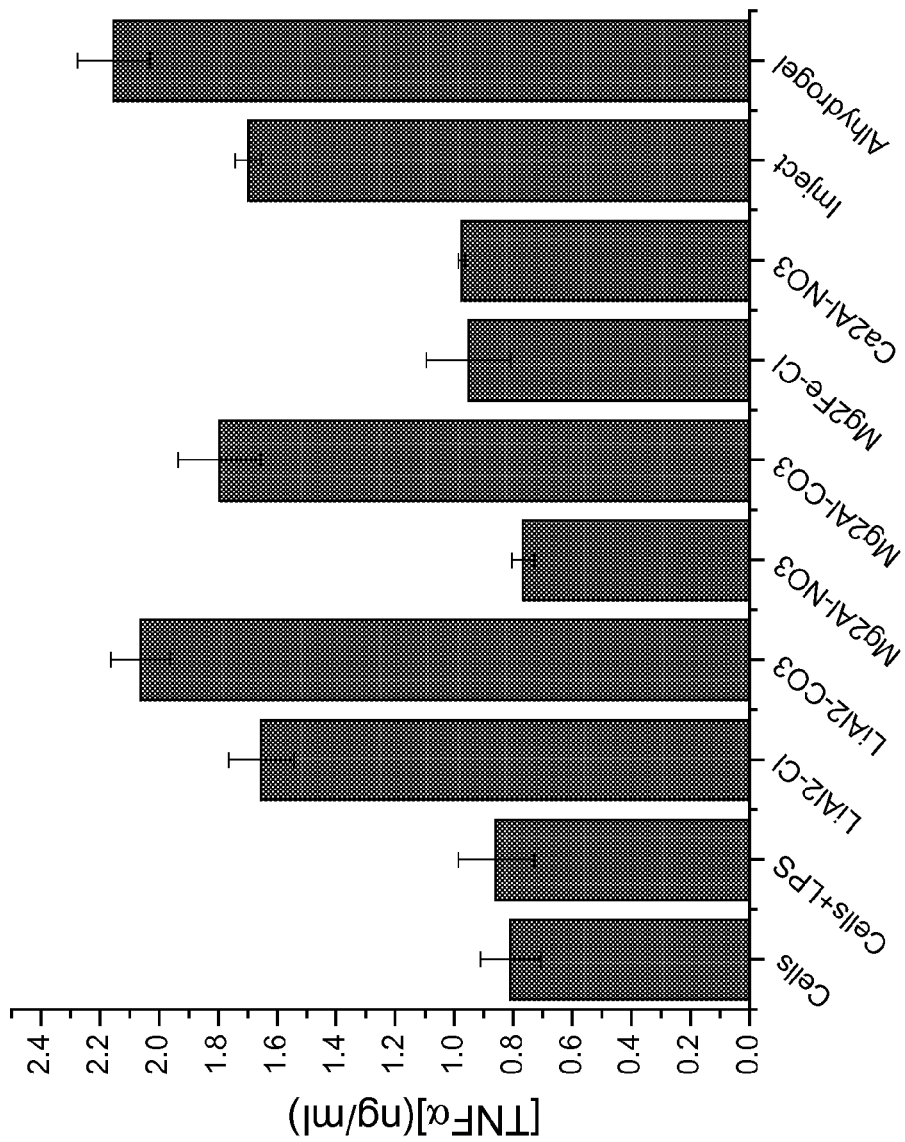

European Patent Office, PCT International Search Report for International Application No. PCT/GB2011/050715 date of completion Sep. 2, 2011.
Besserguenev et al., "Synthesis and Structure of the Gibbsite Intercalation Compounds [LiAl2(OH)6]X {X=Cl, Br. NO3} and [LiAl2(OH)6]Cl-H20 Using Synchrotron X-ray and Neutron Powder Diffraction," The American Chemical Society, 1997, pp. 241-247.
Sideris et al., "Mg/Al Ordering in Layered Double Hydroxides Revealed by Multinuclear NMR Spectroscopy," www.sciencemag.org, vol. 321, Jul. 4, 2008, pp. 113-117.
Williams et al., "New insights into the intercalation chemistry of Al(OH)3," The Royal Society of Chemistry, Dalton Trans., 2011, 40, pp. 6012-6022.

* cited by examiner

Key:
C1 : $Mg_2 Al(OH)_6 NO_3 \cdot xH_2O$
C2 : $Ca_2 Al(OH)_6 NO_3 \cdot xH_2O$
C3 : $Li\ Al_2(OH)_6 CO_3$
C4 : $Mg_2 Al(OH)_6 CO_3$
C5 : $Li Al_2(OH)_6 Cl \cdot xH_2O$
C6 : $Mg_2 Fe(OH)_6 Cl \cdot xH_2O$ C7: $[Mg_2Fe(OH)_6](CO_3)_{0.5} \cdot 2H_2O$ C7: $[Mg_2Fe(OH)_6](CO_3)_{0.5} \cdot 2H_2O$ C7: $[Mg_2Fe(OH)_6](CO_3)_{0.5} \cdot 2H_2O$

IMMUNE MODULATION WITH LONG RANGE ORDERED, LAYERED DOUBLE HYDROXIDES

CROSS-REFERENCE TO RELATED APPLICATIONS

This application is filed under the provisions of 35 U.S.C. §371 and claims the benefit of International Patent Application No. PCT/GB2011/050715, filed on Apr. 11, 2011, entitled "IMMUNE MODULATION", which claims the benefit of priority of GB Application No. 1005931.9, filed on Apr. 9, 2010, the contents of both of which are hereby incorporated by reference herein in their entirety.

The present invention relates to an immune modulator, such as a vaccine adjuvant, and to uses of said modulator in altering (modulating) an immune response, e.g. in stimulating or suppressing a specific immune response. It may have applications for therapeutic or prophylactic purposes.

BACKGROUND TO THE INVENTION

Immune responses are of two general types: innate and adaptive. Generally, innate immune responses are fast and rapid, whereas adaptive immune responses are slower to be induced but subsequently provide immunological memory. Innate responses can trigger inflammation, for example because the cells of innate immunity produce hormone-like ('pro-inflammatory') cytokines such as interleukins (IL-1, IL-6) and tumour necrosis factor (TNF)-alpha. Crucially, innate immune responses are also usually required for the initiation and regulation of adaptive responses.

Innate immune responses can be mediated by cells such as monocytes and macrophages, mast cells, and granulocytes including neutrophils, eosinophils and basophils and NK cells. Innate-like immune responses may also be mediated by cells such as NKT cells, including invariant NKT cells, and gamma-delta T cells.

Dendritic cells (DCs) are specialised cells of immunity that provide an important link between innate and adaptive immune responses. They express a diversity of molecular sensors that enable them to detect and discriminate between different types of 'danger', such as viral or microbial infections, and perhaps cellular damage, whether or not it is caused by an infection. DCs subsequently change their properties in response to the 'danger' (for example they may secrete the cytokine IL-12 and up-regulate expression of co-stimulatory molecules such as CD86, in a process often termed 'activation' or 'maturation'). This enables them to initiate and regulate adaptive immune responses that are typically mediated by lymphocytes.

Adaptive immune responses include specific antibody responses that may, for example, help to clear infectious agents, and cytotoxic T cell responses that may enable killing of infected cells and tumour cells. Antibodies are produced by B lymphocytes (as plasma cells) whereas cytotoxic T cells generally develop from the CD8+ T cell subset (and, perhaps less frequently, from the CD4+ T cell subset).

Immunological interventions can be used, in theory or in practice, to modulate immune responses. Vaccines typically stimulate immune responses against, for example, infectious diseases or cancers. In contrast, other approaches, experimentally or clinically, may suppress aberrant or unwanted immune responses. These include allergies and other immune-related sensitivities (sometimes termed 'hypersensitivity diseases'), autoimmune diseases, and transplantation reactions (including transplant rejection and graft-versus-host disease). Any agent that acts to modulate an immune response, whether by stimulating or suppressing a response, may be termed an immune modulator.

An immunogenic composition is a composition that can be used to modulate immune responses. Such a composition generally comprises an antigen (a substance against which an adaptive immune response may be directed; this response may involve antibodies or cytotoxic T cells, or both) and an immune modulator.

DNA vaccination is known and therefore an antigen may be a macromolecule, such as a polypeptide chain, an RNA preparation that can be translated into a polypeptide chain, or a DNA preparation that encodes a polypeptide chain and that may be transcribed into an RNA intermediate. The antigen may be a DNA plasmid that has been genetically engineered to produce one or more specific polypeptide against which an adaptive immune response may be directed.

Vaccines are a well known type of immunogenic composition and typically contain an antigen, such as a microbial or tumour component against which a specific adaptive immune response is to be directed, and an adjuvant, which mimics a cause of 'danger' and stimulates an appropriate type of adaptive response to be generated.

A series of compounds known collectively to immunologists as 'alums' is known for use as an immune modulator by acting as an adjuvant, which normally stimulates an immune response. The term 'alum' is used very generically, and seems to refer to either boehmite (AlOOH) or amorphous aluminum hydroxyphosphate. It should be noted that the 'alum' of immunologists is very different to that of the physical sciences; when chemists speak of 'alum' they refer to a set of compounds with the formula $AB(SO_4)_2.12H_2O$, such as $KAl(SO_4)_2.12H_2O$. Henceforth, the term 'alum' should be taken to mean the alum of immunologists.

Alum may act as an adjuvant, to stimulate a certain type(s) of immune response. In so doing, it may lead to modulation or suppression of other types of immune response. Alum is the most widely used adjuvant in human vaccines, but the exact mechanism of action remains unknown. Alum is known to have a good effect in terms of inducing antibody responses (B cell responses) but it does not appear to induce significant generation of cytotoxic T cells. This limits its efficacy in applications such as anti-viral and anti-tumour treatments. Further, the exact chemical structure of alum is not well characterised; it would be preferable to use a chemical product that had a clear and well defined structure, chemical composition, and purity.

There is therefore a need for an improved immune modulator, which can act either as an adjuvant or, in other circumstances, as an immune suppressant.

Layered double hydroxides (LDHs) are a class of compounds that comprise two or more metal cations and have a layered structure. LDHs can be represented by the general formulae (1), or (2) or (3):

$$[M^{I}M^{III}_{2}(OH)_{6}][A^{n-}_{1/n}].zH_2O \quad (1)$$

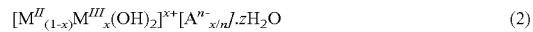

$$[M^{II}_{(1-x)}M^{III}_{x}(OH)_{2}]^{x+}[A^{n-}_{x/n}].zH_2O \quad (2)$$

$$[M^{II}M^{III}_{4}(OH)_{12}][A^{n-}_{2/n}].zH_2O \quad (3)$$

wherein: $M^{I}$, $M^{II}$ and $M^{III}$ are mono, di- and trivalent metal cations respectively (for example, $M^{I}$ may be $Li^{-}$, $M^{II}$ may be $Ca^{2+}$, $Mg^{2+}$, $Ba^{2+}$, $Mn^{2+}$, $Fe^{2+}$, $Co^{2+}$, $Ni^{2+}$, $Cu^{2+}$ $Zn^{2+}$, or $Cd^{2+}$, and $M^{III}$ may be $Al^{3+}$, $Fe^{3+}$, $Cr^{3+}$ $V^{3+}$ or $Co^{3+}$), which cations occupy octahedral positions in hydroxide layers;

$A^{n-}$ is an interlayer charge-compensating anion with a charge of n (where n is an integer, e.g. 1 or 2), and may be inorganic or organic; examples of A are $CO_3^{2-}$, $HCO_3^-$, $NO_3^-$, $Cl^-$, $Br^-$, $SO_4^{2-}$, $F^-$ or $Br^-$;

x is a number less than 1; and z is 0, or a number greater than 0, e.g. from 0.1 to 5, such as from 0.5 to 4.

The values of x have been reported to be from 1/10 to 1/2. However pure phases only exist for values from 1/5 to 1/3; outside this range compounds with different structures are obtained. It has been proposed that for Mg—Al LDHs with high values of x, $Al(OH)_3$ is formed concomitantly with the LDH, due to the increased number of aluminum octahedra (Am. Mineral, 1979, 64, 836).

Therefore, as the skilled reader will appreciate, $M^{II}$ to $M^{III}$ in ratios of 1:1 (x=1/2) would not give rise to a pure LDH product and significant aluminum hydroxide impurities would be present.

A large number of LDHs with a variety of $M^{II}$-$M^{III}$ cation pairs (e.g. Ca—Al) have been reported and studied. Furthermore, it is possible to have LDHs in which there is more than one type of $M^{II}$ and/or more than one type of $M^{III}$ metal ion present. Equally, LDHs having the $M^I$-$M^{III}$ cation pair Li-Al with different anions in the interlayer space have been reported and studied. A review of LDHs is provided in J. Mater. Chem., 2002, 12, 3191-3198.

It has previously been identified that the surface acidity of LDHs is largely affected by the nature of the interlayer anion (J. Mater. Chem., 1998, 8, 1917-1925). This acidity can be measured using Hammett indicators. The order of acidity of Li—Al and Mg—Al based LDHs has been shown to vary with the nature of the anion, such that carbonate<nitrate<chloride in terms of acidity. The Li—Al and Mg—Al LDHs intercalated with chloride and nitrate exhibited pKa values in the region of 0.1 up to 5.2, whilst those intercalated with carbonate had pKa values above 12.2. Thus anions which are the conjugate bases of weaker acids provide LDHs that are more basic.

Carbonate intercalated LDHs have generally been found to contain basic sites with pKa values in the range of 10.7 to 13.3 and a few sites with a pKa of 16.5 (J. Catal., 1992, 134, 58).

SUMMARY OF THE INVENTION

The present invention provides, in a first aspect, a layered double hydroxide of formula (I), (II) or (III), as defined below, for use in modulating an immune response to an antigen.

The modulation may be an increased or a decreased immune response and may be caused in an animal; in particular a human, another mammal, or a bird or a fish. The modulation in immune response may be modulation of any one or more aspect of an innate immune response or an adaptive immune response. The modulation in immune response may, for example, be modulation of any one or more aspect of an immune response selected from: activation of dendritic cells, the generation of pro-inflammatory cytokines, the generation of antibodies, the generation of cytotoxic T-cells, or the generation of a response by other immune cells. The modulation may be modulation of an immune response involving dendritic cells, monocytes, macrophages, mast cells, granulocytes, including neutrophils, eosinophils and basophils, NK cells, NKT cells, including invariant NKT cells, or gamma-delta T cells. The modulation may, for example, comprise increased or decreased stimulation of NK cells or neutrophils, or may comprise enhanced or decreased NO production, reactive O2 production or phagocytic activity.

The modulation in immune response may result from a direct or indirect action of the layered double hydroxide of formula (I), (II) or (III), as defined below, on any cell of innate or adaptive immunity, including cell types selected from: dendritic cells, monocytes, macrophages, mast cells, granulocytes, including neutrophils, eosinophils and basophils, NK cells, NKT cells, including invariant NKT cells, and gamma-delta T cells.

The invention therefore provides an immune modulator comprising a layered double hydroxide of formula (I), (II) or (III).

The LDH of formula (I), (II) or (III) is therefore provided for use in the treatment or prevention of a medical condition by modulating an immune response to an antigen. The medical condition may be selected from infectious diseases; allergies and other immune-related sensitivities; autoimmune diseases; transplantation reactions; proliferative diseases; and other inflammatory conditions. The medical conditions that may be treated or prevented are discussed in more detail below.

The LDHs used in the invention are of formula (I), formula (II), or formula (III)

  (I)

  (II)

  (III)

in which $M^I$ is $Li^+$, $M^{II}$ is a divalent metal cation or a mixture of two or more divalent metal cations, $M^{III}$ is a trivalent metal cation or a mixture of two or more trivalent metal cations, or a mixture of one or more trivalent metal cation with one or more quadravalent metal cation, x is from 1/5 to 1/3, and A is an interlayer anion having a charge n, wherein optionally some or all of the interlayer anion A may be replaced by one or more biologically active agent(s) and/or one or more antigen(s), and wherein A is selected from conjugate bases of acids having a pKa of 1 or higher, except for in LDHs of formula (II) when $M^{II}$ comprises $Ca^{2-}$ and in LDHs of formula (I), wherein A is selected from conjugate bases of acids having a pKa of −4 or higher.

Preferably, $M^{II}$ is selected from: $Ca^{2+}$, $Mg^{2+}$, $Mn^{2+}$, $Fe^{2+}$, $Co^{2+}$, $Ni^{2+}$, $Cu^{2+}$ $Zn^{2+}$, and $Cd^{2+}$, and mixtures thereof; and mixtures of one or more of $Ca^{2+}$, $Mg^{2+}$, $Mn^{2+}$, $Fe^{2+}$, $Co^{2+}$, $Ni^{2+}$, $Cu^{2+}$ $Zn^{2+}$, and $Cd^{2+}$ together with one or both of $Pd^{2+}$ and $Pt^{2+}$.

Preferably, $M^{III}$ is selected from: $Al^{3+}$, $Fe^{3+}$, $Cr^{3+}$ $V^{3+}$ $Co^{3+}$, $Ga^{3+}$, $In^{3+}$ and $Sc^{3+}$ and mixtures thereof; and mixtures of one or more of $Al^+$, $Fe^{3+}$, $Cr^{3+}$ $V^{3+}$ $Co^{3+}$, $Ga^{3+}$, $In^{3+}$ and $Sc^{3+}$ together with one or more of $Y^{3+}$, $Rh^{3+}$, $Ir^{3+}$ and $Zr^{4+}$.

The compounds of formula (I) or formula (II) or formula (III) may optionally be hydrated. The amount of water of hydration may be a stoichiometric amount or a non-stoichiometric amount. In one embodiment, there may be from 0.1 to 5, such as from 0.5 to 4, molecules of water per LDH formula unit.

The compounds of formula (I) or formula (II) or formula (III) may be non-calcined LDHs or may be calcined LDHs.

Surprisingly, it has been found that these layered double hydroxides act to modulate an immune response. The effect has been shown in terms of an effect on dendritic cell activation, an effect on T cell response and an effect on antibody induction. Therefore, surprisingly, the layered double hydroxides of the invention can potentially be used in a variety of applications where immune modulation is required. This range of applications is wider than those for which alum can be used, as the induced response with LDHs is not limited primarily to an antibody response, as it is with alum. Further, LDHs have well defined structure, chemical composition, and purity, making them suitable for medical applications.

New, more efficient adjuvants would permit less material to be used as antigen(s) in the preparation of immunogenic compositions, such as vaccines. This is advantageous because if only small quantities of material are required, a new vaccine for a new threat, e.g. pandemic flu, can be prepared more quickly.

The layered double hydroxide of formula (I), (II) or (III) as defined above, for use in modulating an immune response to an antigen, may be administered to a patient together with said antigen. The LDH and antigen may be administered simultaneously, sequentially (in either order) or separately (in either order). When administered separately there may be a time delay between administering the two components of, for example, 15 minutes or more, such as 30 minutes or more. Preferably they are administered simultaneously or sequentially.

The invention provides, in a second aspect, an immune modulator composition comprising (i) a layered double hydroxide of formula (I), (II) or (III) as defined above and (ii) an antigen. The composition may be an immunogenic composition for use in eliciting an increased or a decreased immune response to an antigen in an animal; in particular a human, another mammal, or a bird or a fish.

The invention provides, in a third aspect, an immune modulator kit comprising (i) a layered double hydroxide of formula (I) or (II) or (III) as defined above and (ii) an antigen, to be administered simultaneously, sequentially or separately. The kit may be for use in eliciting an increased or a decreased immune response to an antigen in an animal; in particular a human, another mammal, or a bird or a fish. The kit may include instructions to administer the layered double hydroxide and the antigen, simultaneously, sequentially or separately, to a subject in need of immune modulation. The components may be administered simultaneously, sequentially (in either order) or separately (in either order). When administered separately there may be a time delay between administering the two components of, for example, 15 minutes or more, such as 30 minutes or more. Preferably they are administered simultaneously or sequentially.

The invention provides, in a fourth aspect, the use of a layered double hydroxide of formula (I), (II) or (III) as defined above in the manufacture of a medicament for modulating an immune response to an antigen. The medicament may be for increasing or decreasing an immune response in an animal; in particular a human, another mammal, or a bird or a fish. The medicament may optionally further comprise an antigen or the medicament may be provided for administration with an antigen, simultaneously, sequentially (in either order) or separately (in either order). When administered separately there may be a time delay between administering the two components of, for example, 15 minutes or more, such as 30 minutes or more. Preferably they are administered simultaneously or sequentially.

The invention therefore provides a method of modulating an immune response in a subject, comprising administering to said subject a layered double hydroxide of formula (I), (II) or (III) as defined above. The layered double hydroxide may be provided in the form of an immune modulator composition comprising (i) the layered double hydroxide and (ii) an antigen. Alternatively, the layered double hydroxide may be administered to the subject with an antigen, with the administration being simultaneous, sequential or separate.

The invention provides, in a fifth aspect, the use of a layered double hydroxide of formula (I), (II) or (III) as defined above in the manufacture of a medicament for preventing or treating a medical condition selected from the group comprising: infectious diseases; allergies and other immune-related sensitivities (hypersensitivity diseases); autoimmune diseases; transplantation reactions (including transplant rejection and graft versus host disease); proliferative diseases including cancers; and other inflammatory conditions (including autoinflammatory conditions). The medicament may be for preventing the disease in an animal; in particular a human or another mammal, or a bird or a fish. The medicament may optionally further comprise an antigen or the medicament may be provided for administration with an antigen, simultaneously, sequentially (in either order) or separately (in either order). When administered separately there may be a time delay between administering the two components of, for example, 15 minutes or more, such as 30 minutes or more. Preferably they are administered simultaneously or sequentially.

The invention therefore provides a method of preventing or treating a medical condition selected from the group comprising: infectious diseases; allergies and other immune-related sensitivities (hypersensitivity diseases); autoimmune diseases; transplantation reactions (including transplant rejection and graft versus host disease); proliferative diseases (including cancers); and other inflammatory conditions (including autoinflammatory conditions). The method comprises administering to said subject a layered double hydroxide of formula (I), (II) or (III) as defined above. The layered double hydroxide may be provided in the form of an immune modulator composition comprising (i) the layered double hydroxide and (ii) an antigen. Alternatively, the layered double hydroxide may be administered to the subject with an antigen, with the administration being simultaneous, sequential or separate.

The invention provides, in a sixth aspect, a method of preparing an immune modulator composition comprising the step of combining (i) a layered double hydroxide of formula (I), (II) or (III) as defined above and (ii) an antigen.

The invention provides, in a seventh aspect, a method of obtaining a treated dendritic cell product, the method comprising: combining dendritic cells with (i) a layered double hydroxide of formula (I), (II) or (III) as defined above and (ii) an antigen. The layered double hydroxide and antigen may be provided in the form of an immune modulator composition comprising (i) the layered double hydroxide and (ii) an antigen and this composition may then be combined with the dendritic cells. Alternatively, the layered double hydroxide and the antigen may be provided separately and these separate components may be combined with the dendritic cells in any order. The dendritic cells may have been generated from a subject's blood monocytes or may have been generated from other precursors, for example from dendritic cell progenitors from the subject's bone marrow.

The treated dendritic cells thus obtained can be administered to the subject to prevent or treat a medical condition. The condition may be selected from the group comprising: infectious diseases; allergies and other immune-related sensitivities (hypersensitivity diseases); autoimmune diseases; transplantation reactions (including transplant rejection and graft versus host disease); proliferative diseases including cancers; and other inflammatory conditions (including autoinflammatory conditions). This re-administration can be of the treated dendritic cells together with some or all of the layered double hydroxide and antigen, or the re-administration can be after separating the dendritic cells from the layered double hydroxide and antigen.

As the skilled reader will appreciate, "adoptive cell therapies" are known. These involve combining dendritic cells with antigen and a stimulus and administering the dendritic cells to the subject. The dendritic cells will generally have been generated from the subject's blood monocytes but may be generated from other precursors, for example from dendritic cell progenitors from the subject's bone marrow.

Therefore in accordance with the present invention an immune modulator composition can be created that comprises (i) a layered double hydroxide of formula (I), (II) or (III) as defined above and (ii) an antigen and (iii) dendritic cells. The dendritic cells may suitably have been generated from the subject, e.g. from the subject's blood monocytes or from dendritic cell progenitors from the subject's bone marrow. The dendritic cells from such a composition can subsequently be administered to the subject to treat or prevent a medical condition. This administration can be together with the layered double hydroxide and antigen or can be after separating the dendritic cells from some or all of the layered double hydroxide and antigen.

The invention provides, in an eighth aspect, a method of obtaining a treated T cell product, the method comprising: combining T cells with dendritic cells that have already been contacted with (i) a layered double hydroxide of formula (I), (II) or (III) as defined above and (ii) an antigen. The T cells may suitably have been generated from the subject, e.g. from peripheral blood of the subject.

The treated T cells thus obtained can be administered to the subject to prevent or treat a medical condition. The condition may be selected from the group comprising: infectious diseases; allergies and other immune-related sensitivities (hypersensitivity diseases); autoimmune diseases; transplantation reactions (including transplant rejection and graft versus host disease); proliferative diseases including cancers; and other inflammatory conditions (including autoinflammatory conditions). This administration can be of the treated T cells together with the dendritic cells, or the administration can be after separating the T cells from some or all of the dendritic cells.

The method may comprise the steps of: (a) combining dendritic cells with (i) a layered double hydroxide of formula (I), (II) or (III) as defined above and (ii) an antigen; and then (b) combining the dendritic cells with the T cells.

In step (a) the layered double hydroxide and antigen may be provided in the form of an immune modulator composition comprising (i) the layered double hydroxide and (ii) an antigen and this composition may then be combined with the dendritic cells. Alternatively, the layered double hydroxide and the antigen may be provided separately and these separate components may be combined with the dendritic cells in any order.

In step (b) the dendritic cells may be combined with the T cells together with the layered double hydroxide and antigen, or the dendritic cells can be combined with the T cells after separating the dendritic cells from some or all of the layered double hydroxide and antigen.

After step (b) the T cells may optionally be separated from some or all of the dendritic cells and/or any other components present (e.g. the layered double hydroxide and antigen). Therefore the treated T cells may be provided on their own, or may be in the form of a composition comprising the T cells together with one or more of: dendritic cells, layered double hydroxide and antigen.

Therefore in accordance with the present invention an immune modulator composition can be created that comprises (i) a layered double hydroxide of formula (I), (II) or (III) as defined above and (ii) an antigen and (iii) dendritic cells and (iv) T cells. The T cells from such a composition can subsequently be administered to the subject to treat or prevent a medical condition. The dendritic cells may suitably have been generated from the subject, e.g. from the subject's blood monocytes or from dendritic cell progenitors from the subject's bone marrow. The T cells may suitably have been generated from the subject, e.g. from peripheral blood of the subject.

Also provided is a treated dendritic cell product as obtained by the method of the seventh aspect, or a treated T cell product as obtained by the method of the eighth aspect, for use in preventing or treating a medical condition. The condition may be selected from the group comprising: infectious diseases; allergies and other immune-related sensitivities (hypersensitivity diseases); autoimmune diseases; transplantation reactions (including transplant rejection and graft versus host disease); proliferative diseases including cancers; and other inflammatory conditions (including autoinflammatory conditions).

Thus the invention provides a method of preventing or treating a medical condition selected from the group comprising: infectious diseases; allergies and other immune-related sensitivities (hypersensitivity diseases); autoimmune diseases; transplantation reactions (including transplant rejection and graft versus host disease); proliferative diseases (including cancers); and other inflammatory conditions (including autoinflammatory conditions). The method comprises administering to said subject a treated dendritic cell product as obtained by the method of the seventh aspect, or a treated T cell product as obtained by the method of the eighth aspect.

In a ninth aspect, the invention provides the use of a layered double hydroxide of formula (I), (II) or (III) as defined above to assess a subject's immune response. This assessment may, for example, be by measuring the responsiveness of the subject's immune cells to the LDH, or to a composition comprising the LDH. The LDH may therefore be used as an in vitro, in vivo or ex vivo assay to evaluate an immune response. The assay may be used to evaluate the strength of the subject's immune system, or may be used to evaluate whether the subject's immune system is compromised (for example by a disease, or by environmental conditions, or due to a treatment, e.g. a surgical treatment, a drug treatment, or other therapeutic treatment). It may be that the LDH, or a composition comprising the LDH, may be placed on the skin of a subject.

Therefore the invention provides a method for assessing a subject's immune response that comprises the steps of: bringing immune cells of the subject into contact with a layered double hydroxide of formula (I), (II) or (III) as defined above; and measuring the response of the immune cells. The method may be carried out by adding a layered double hydroxide of formula (I), (II) or (III) as defined above to cells in vitro, in vivo or ex vivo. The method may further involve comparing the response of the immune cells to another response, e.g. a standard or baseline or a previously measured response for the same subject.

DETAILED DESCRIPTION OF THE INVENTION

All of the following preferred features apply to all of the above aspects of the invention, as appropriate.

A first preferred class of LDH compound that can be used in the invention is of formula (I) wherein $M^I$ is $Li^+$ and $M^{III}$ comprises $Al^{3+}$ or a mixture of $Al^{3+}$ with $Fe^3$ and A is an interlayer anion having a charge n wherein A is selected from conjugate bases of acids having a pKa of −4 or higher. A may, for example, be selected from $Cl^-$, $SO_4^{2-}$, $NO_3^{2-}$, $CO_3^{2-}$, $HO^-$, $HOO^-$, $ClO^-$, $HCO_3^-$, or conjugate bases of organic acids.

These compounds are optionally, but preferably, hydrated. The amount of water of hydration may be a stoichiometric amount or a non-stoichiometric amount.

Most preferably, in the LDH of formula (I) $M^{III}$ is $Al^{3+}$.

The LDHs of formula (I) may have any surface pKa, such as a surface pKa of 1 or more, 2 or more, 3 or more, 4 or more or 5 or more. However, it is preferred that for LDHs of formula (I) the surface pKa is greater than 5.2, such as 5.5 or higher, 6 or higher, 7 or higher, 8 or higher, 9 or higher, or 10 or higher.

Without being bound by theory, it is believed that different LDHs with different physicochemical properties may act on cells such as dendritic cells at the cell surface, or in intracellular compartments such as phagosomes or other endosomes, the cytosol or the nucleus. Again, without being bound by theory, LDHs with higher surface pKa values may act as a buffer and arrest maturation. Such LDHs could facilitate cross presentation resulting in a cytotoxic T cell response. As the skilled reader will appreciate, cross presentation is when antigens from the extracellular environment (rather than peptides derived from proteins synthesised by the cell itself) are presented on major histocompatibility complex (MHC) I molecules and stimulate CD8+ T cell immunity. Finally, (again not being bound by theory) higher surface pKa values may stimulate molecular sensors in the cytosol.

LDHs based on $[LiAl_2(OH)_6]^+$ have a surface pKa of about 5 or less when the anion is $Cl^-$ or $NO_3^-$.

To achieve the preferred surface pKa values of greater than 5.2, A should therefore be the conjugate base of an acid that is weaker than nitric acid or hydrochloric acid, which have pKa values of −1 and −4 respectively. Accordingly, it can be preferred that A is the conjugate base of an acid that has a pKa value of greater than −1.

The surface pKa of an LDH may be measured by a Hammett indicator test. This may involve adding 2 ml of Hammett indicator, dissolved in benzene or dichloromethane, to 0.2 g of a finely powdered sample of the LDH, shaking the sample, and then noting the colour change. pKa values for acids are well known in the art and references in this regard are intended as reference to pKa values for acids at room temperature (25° C.).

Preferably, for LDHs of formula (I), A is selected from anions of an acid having a pKa of 2 or higher, more preferably 3 or higher. A may therefore suitably be selected from conjugate bases of weak acids, such as hydroxide anions, peroxide anions, hypochlorite anions, carbonate or bicarbonate anions, or conjugate bases of organic acids. For example, A may be selected from $CO_3^{2-}$, $HO^-$, $HOO^-$, $ClO^-$, $HCO_3^-$, $RCOO^-$, $R(COO^-)_2$. In one embodiment, A may be carbonate, bicarbonate, formate, acetate, lactate, oxalate or succinate.

In relation to the present invention, wherever reference is made to $RCOO^-$ or $R(COO^-)_2$, the following definitions and preferred definitions apply. R is hydrogen, alkyl having 1-24 carbon atoms (e.g. 1-20 carbon atoms or 1-16 carbon atoms or 1-12 carbon atoms), alkenyl having 2-24 carbon atoms (e.g. 2-20 carbon atoms or 2-16 carbon atoms or 2-12 carbon atoms), cycloalkyl having 3-8 carbon atoms, aryl having 6-14 carbon atoms, or carboxy or carboxyalkyl having 1-24 carbon atoms (e.g. 1-20 carbon atoms or 1-16 carbon atoms or 1-12 carbon atoms), and wherein one or more hydrogen atom in any of the aforesaid groups may optionally be substituted with one or more substituent group, such as a halide (e.g. Cl), nitro, amino, ethyl, phosphate, amide or hydroxy group. Preferred definitions for R are H, alkyl having 1-6 (e.g. 1-4) carbon atoms, aryl having 6 carbon atoms, or carboxy or carboxyalkyl having 1-6 (e.g. 1-4) carbon atoms, and wherein one or more hydrogen atom in any of the aforesaid groups may optionally be substituted with one or more substituent group, such as a halide (e.g. Cl), nitro, amino, ethyl, phosphate, amide or hydroxy group.

A second preferred class of LDH compound that can be used in the invention is of formula (II) wherein $M^{II}$ is a divalent metal cation selected from $Ca^{2+}$, $Mg^{2+}$, $Mn^{2+}$, $Fe^{2+}$, $Co^{2+}$, $Ni^{2+}$, $Cu^{2+}$ or $Zn^{2+}$, $M^{III}$ is a trivalent metal cation selected from $Al^{3+}$, $Fe^{3+}$, $Cr^{3+}$, $V^{3+}$ $Co^{3+}$, $Ga^{3+}$, or $In^{3+}$, x is from ⅕ to ⅓ and A is an interlayer anion having a charge n, wherein A is selected from conjugate bases of acids having a pKa of 1 or higher, except for when $M^{II}$ is $Ca^{2+}$, when A is selected from conjugate bases of acids having a pKa of −4 or higher.

Such compounds are optionally, but preferably, hydrated. The water of hydration, if present, may be present in a stoichiometric amount or a non-stoichiometric amount.

In the LDHs of formula (II) the selection of A is affected by the nature of $M^{II}$; it has been found that a larger $M^{II}$ cation, such as $Ca^{2+}$, permits the use of an anion from a stronger acid. For $Ca^{2+}$, A may be selected from conjugate bases of weak acids, such as hydroxide anions, peroxide anions, hypochlorite anions, carbonate or bicarbonate anions, or conjugate bases of organic acids, or may be selected from conjugate bases of strong acids, such as chloride, bromide, iodide, sulfate or nitrate anions. For other, smaller, $M^{II}$ cations A may be selected from conjugate bases of weak acids, such as hydroxide anions, peroxide anions, hypochlorite anions, carbonate or bicarbonate anions, or conjugate bases of organic acids.

The LDHs of formula (II) may have any surface pKa, such as a surface pKa of 1 or more, 2 or more, 3 or more, 4 or more or 5 or more. It is preferred that for the LDHs of formula (II) the surface pKa is greater than 5.2, such as 5.5 or higher, 6 or higher, 7 or higher, 8 or higher, 9 or higher, or 10 or higher.

Without being bound by theory, it is believed that different LDHs with different physicochemical properties may act on cells such as dendritic cells at the cell surface, or in intracellular compartments such as phagosomes or other endosomes, the cytosol or the nucleus. Again without being bound by theory, LDHs with higher surface pKa values may act as a buffer and arrest maturation. Alternatively, again not being bound by theory, higher surface pKa values may stimulate molecular sensors in the cytosol.

It is known that the surface pKa of LDHs based on $[Mg_2Al(OH)_6]^+$ have a surface pKa of about 5 or less when the anion is $Cl^-$ or $NO_3^-$.

To achieve the desired higher pKa values in the LDHs of formula (II), when the LDH is based on a smaller $M^{II}$ cation, such as $Mg^{2+}$, A should be the conjugate base of an acid that is weaker than nitric acid or hydrochloric acid, which have pKa values of −1 and −4 respectively. However, when the LDH of formula (II) is based on the larger $Ca^{2+}$ $M^{II}$ cation, A can be the conjugate base of stronger acids whilst still achieving a desired surface pKa.

In one embodiment, $M^{II}$ is selected from $Mg^{2+}$, $Mn^{2+}$, $Fe^{2+}$, $Co^{2+}$, $Ni^{2+}$, $Cu^{2+}$ or $Zn^{2+}$ (preferably $Mg^{2+}$, $Zn^{2+}$ $Co^{2+}$, $Cu^{2+}$ and $Ni^{2-}$, most preferably $Mg^{2+}$, $Zn^{2+}$ and $Ni^{2+}$) and A is selected from conjugate bases of acids having a pKa of 1 or higher, preferably 2 or higher, more preferably 3 or higher. A may therefore suitably be selected from conjugate bases of weak acids, such as hydroxide anions, peroxide anions, hypochlorite anions, carbonate or bicarbonate anions, or conjugate bases of organic acids. For example, A may be selected from $CO_3^{2-}$, $HO^-$, $HOO^-$, $ClO^-$, $HCO_3^-$, $RCOO^-$, $R(COO^-)_2$ wherein R is as defined above. In one embodiment, A may be carbonate, bicarbonate, formate, acetate, lactate, oxalate or succinate. Preferably $M^{III}$ is $Al^{3+}$ in this embodiment. However, $M^{III}$ could suitably be selected from $Al^{3+}$, $Fe^{3+}$ and $Ga^{3+}$ in this embodiment; for example $M^{III}$ could be $Fe^{3+}$ in this embodiment.

Therefore it may be that $M^{II}$ is selected from $Mg^{2+}$, $Zn^{2+}$, $Co^{2+}$, $Cu^{2+}$ and $Ni^{2+}$ (preferably $Mg^{2+}$, $Zn^{2+}$ and $Ni^{2+}$) and A is selected from $CO_3^{2-}$, $HO^-$, $HOO^-$, $ClO^-$, $HCO_3^-$, $RCOO^-$, and $R(COO^-)_2$ wherein R is as defined above (preferably carbonate, bicarbonate, formate, acetate, lactate, oxalate or succinate), and $M^{III}$ is selected from $Al^{3+}$, $Fe^{3+}$ and $Ga^{3+}$ (preferably $Al^{3+}$ or $Fe^{3+}$; most preferably $Al^{3+}$).

In another embodiment, $M^{II}$ is $Ca^{2+}$ and A is selected from conjugate bases of acids having a pKa of −4 or higher. A may, for example, be selected from $Cl^-$, $SO_4^{2-}$, $NO_3^{2-}$, $CO_3^{2-}$, $HO^-$, $HOO^-$, $ClO^-$, $HCO_3^-$, or conjugate bases of organic acids. A may in one such embodiment be selected from conjugate bases of acids having a pKa of −2 or higher, such as −1 or higher. For example, A may be nitrate, carbonate, bicarbonate, formate, acetate or lactate. It may be that A is selected from conjugate bases of acids having a pKa of 1 or higher, more preferably 2 or higher, such as 3 or higher. For example, A may be selected from $CO_3^{2-}$, $HO^-$, $HCO_3^-$, $RCOO^-$, $R(COO^-)_2$ where R is as defined above. Preferably $M^{III}$ is $Al^{3+}$, $Ga^{3+}$, or $Fe^{3+}$ in this embodiment. Most preferably $M^{III}$ is $Al^{3+}$ in this embodiment.

In this embodiment, where $M^{II}$ is $Ca^{2+}$ and $M^{III}$ is $Al^{3+}$, even when A is a conjugate base of a strong acid, such as $NO_3^{2-}$, the surface pKa of the LDH has been found to be basic.

In one preferred embodiment of the second class of LDH compound, $M^{II}$ is selected from $Ca^{2+}$, $Mg_{2+}$, $Zn^{2+}$ $Co^{2+}$, $Cu^{2+}$ and $Ni^{2+}$, most preferably from $Ca^{2+}$, $Mg^{2+}$, $Zn^{2+}$ and $Ni^{2+}$, Preferably $M^{III}$ is $Al^{3+}$.

A third preferred class of LDH compound that can be used in the invention is of formula (III) wherein $M^{II}$ is a divalent metal cation selected from $Co^{2+}$, $Ni^{2+}$, $Cu^{2+}$ or $Zn^{2+}$, $M^{III}$ is $Al^{3+}$, and A is an interlayer anion having a charge n, wherein A is selected from conjugate bases of acids having a pKa of 1 or higher.

Such compounds are optionally, but preferably, hydrated. The water of hydration, if present, may be present in a stoichiometric amount or a non-stoichiometric amount.

A may be selected from conjugate bases of weak acids, such as hydroxide anions, peroxide anions, hypochlorite anions, carbonate or bicarbonate anions, or conjugate bases of organic acids.

The LDHs of formula (III) may have any surface pKa, such as a surface pKa of 1 or more, 2 or more, 3 or more, 4 or more or 5 or more. It is preferred that for the LDHs of formula (III) the surface pKa is greater than 5.2, such as 5.5 or higher, 6 or higher, 7 or higher, 8 or higher, 9 or higher, or 10 or higher.

To achieve the desired higher pKa values in the LDHs of formula (III), A should preferably be the conjugate base of an acid that is weaker than nitric acid or hydrochloric acid, which have pKa values of −1 and −4 respectively.

In one embodiment, $M^{II}$ is selected from $Co^{2+}$, $Ni^{2+}$, $Cu^{2+}$ or $Zn^{2+}$ (preferably $Zn^{2+}$ and $Ni^{2+}$) and A is selected from conjugate bases of acids having a pKa of 1 or higher, preferably 2 or higher, more preferably 3 or higher. A may therefore suitably be selected from conjugate bases of weak acids, such as hydroxide anions, peroxide anions, hypochlorite anions, carbonate or bicarbonate anions, or conjugate bases of organic acids. For example, A may be selected from $CO_3^{2-}$, $HO^-$, $HOO^-$, $ClO^-$, $HCO_3^-$, $RCOO^-$, $R(COO^-)_2$ wherein R is as defined above. In one embodiment, A may be carbonate, bicarbonate, formate, acetate, lactate, oxalate or succinate. $M^{III}$ is $Al^{3+}$ in this embodiment.

In one embodiment, the LDH compound of the invention is of formula (I), (II) or (III) and has a surface pKa that is 6 or higher, or 7 or higher, or 8 or higher, or 9 or higher, or 10 or higher.

Carbonate intercalated LDHs have generally been found to contain basic sites with pKa values in the range of 10.7 or higher, such as from 10.7 to 13.3. LDHs intercalated with anions of other weak acids would be expected to have similar pKa values.

The LDHs of the present invention may be stoichiometric (i.e. LDHs where the actual ratios of $M^{II}$ to $M^{III}$ or of $M^{I}$ to $M^{III}$ in the LDH are integer values) or may be non-stoichiometric.

A long-range ordered (i.e. non-random) arrangement of cations in the LDH occurs in a preferred embodiment of the present invention. When reference is made to ordering in the present invention it relates to 'long-range' ordering as compared to 'local' ordering. The extent to which ordering is seen is dependent on the choice of metal cations and their relative ratios.

Long-range ordered cation layers can be achieved in stoichiometric LDHs (i.e. LDHs where the actual ratios of $M^{II}$ to $M^{III}$ or of $M^{I}$ to $M^{III}$ in the LDH are integer values) where the ratio of $M^{II}$ to $M^{III}$ is 2:1 (class (II)) or 1:4 (class (III)) or where the ratio of $M^{I}$ to $M^{III}$ is 1:2 (class (I)). These long-range ordered stoichiometric materials can therefore be written as: $M^I_1M^{III}_2(OH)_6]^+[A^{n-}_{1/n}]$ or $[M^{II}_2M^{III}_1(OH)_{12}]^+[A^{n-}_{2/n}]$ or $[M^{II}_1M^{III}_4(OH)_{12}]^+[A^{n-}_{2/n}]$.

Long-range ordering may also be seen in non-stoichiometric derivatives of LDH materials where the calculated ratio of $M^{II}:M^{III}$ is about 1:4 (such as from 1:3.7 to 1:4.3, e.g. from 1:3.8 to 1:4.2), or the calculated ratio of $M^I:M^{III}$ is about 1:2 (such as from 1:1.7 to 1:2.3, e.g. from 1:1.8 to 1:2.2). Non-stoichiometric derivatives have ratios in the LDH of $M^{II}:M^{III}$ or $M^I:M^{III}$ in that are non-integer, e.g. 0.9:4 or 0.5:2. Examples of non-stoichiometric LDH materials that have long-range ordering include $[M^I_{0.9}M^{III}_2(OH)_6]^+[A^{n-}_{1/n}]$ and $[M^{II}_{0.9}M^{III}_4(OH)_{12}]^+[A^{n-}_{2/n}]$ and $[M^I_{0.5}M^{III}_2(OH)_6]^+[A^{n-}_{1/n}]$ and $[M^{II}_{0.5}M^{III}_4(OH)_{12}]^+[A^{n-}_{2/n}]$.

Accordingly, the LDHs used in the present invention may, in one embodiment, be LDHs where the ratio of $M^{II}$ to $M^{III}$ is 2:1 or 1:4 or the ratio of $M^I$ to $M^{III}$ is 1:2, or may be non-stoichiometric derivatives of LDHs where the $M^{II}:M^{III}$ ratio is about 1:4, or the $M^I:M^{III}$ ratio is about 1:2.

In one preferred embodiment of the invention, the LDHs are of formula (I) or (III), or formula (II) where x is ⅓.

As the skilled reader will appreciate, some long-range ordered LDHs exhibit a higher degree of ordering than others. In particular, long-range ordered LDHs based on Mg (e.g. a 2:1 Mg—Al LDH of formula (II)) are not highly ordered, whereas long-range ordered LDHs based on Ca and Li (e.g. a 2:1 Ca—Al LDH of formula (II) or a 1:2 Li—Al LDH of formula (I)) are highly ordered. Generally, the more highly ordered LDHs are preferred but it will be appreciated that a good effect can also be seen with all other long-range ordered LDHs.

Further, for those long-range ordered LDHs that exhibit a higher degree of ordering it has been determined that a good effect can be exhibited even when the LDH's surface pKa is lower. In other words, for those long-range ordered LDHs that exhibit a higher degree of ordering a slightly acidic or neutral surface pKa will still give good results. Therefore it is possible to utilise an anion A with these highly long-range ordered LDHs that is the conjugate base of a stronger acid.

Therefore, for example, long-range ordered LDHs based on Ca or Li (e.g. a 2:1 Ca—Al LDH of formula (II) or a 1:2 Li—Al LDH of formula (I)) can give good results when the surface pKa is 5 or less, e.g. from 1 to 5 or from 2 to 5, as well as when the surface pKa is higher, e.g. 5.2 or higher. Therefore in the case of these highly long-range ordered LDHs A may be selected from conjugate bases of acids having a pKa of −4 or higher and good results will still be achieved.

The best results for anions A that are conjugate bases of stronger acids (e.g. conjugate bases of acids having a pKa of from −4 to 1) are achieved when the LDH is of formula (II) with $M^{II}$ as $Ca^{2+}$ and a $M^{II}:M^{III}$ ratio of 2:1. The combination of the high long-range ordering and the larger cation size of the $Ca^{2+}$ in such products gives excellent results. Of course, excellent results are also achieved for these LDHs when the anion A is selected as a conjugate base of a weaker acid (e.g. conjugate bases of acids having a pKa of 1 or higher).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Mg^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Mg^{2+}$ | $Fe^{3+}$ | $CO_3^{2-}$, $HO^-$, $HOO^-$, $ClO^-$, $HCO_3^-$, $RCOO^-$, $R(COO^-)_2$ (R as defined above) |
| $Ca^{2+}$ | $Al^{3+}$ | $Cl^-$, $SO_4^{2-}$, $NO_3^{2-}$, $CO_3^{2-}$, $HO^-$, $HOO^-$, $ClO^-$, $HCO_3^-$, $RCOO^-$, $R(COO^-)_2$ (R as defined above) |
| $Ca^{2+}$ | $Ga^{3+}$ | $Cl^-$, $SO_4^{2-}$, $NO_3^{2-}$, $CO_3^{2-}$, $HO^-$, $HOO^-$, $ClO^-$, $HCO_3^-$, $RCOO^-$, $R(COO^-)_2$ (R as defined above) |
| $Ca^{2+}$ | $Fe^{3+}$ | $Cl^-$, $SO_4^{2-}$, $NO_3^{2-}$, $CO_3^{2-}$, $HO^-$, $HOO^-$, $ClO^-$, $HCO_3^-$, $RCOO^-$, $R(COO^-)_2$ (R as defined above) |
| $Zn^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Ni^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Co^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Cu^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |

Preferably, $x=\frac{1}{3}$ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Mg^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Ca^{2+}$ | $Al^{3+}$ | $Cl^-$, $SO_4^{2-}$, $NO_3^{2-}$, $CO_3^{2-}$, $HO^-$, $HOO^-$, $ClO^-$, $HCO_3^-$, $RCOO^-$, $R(COO^-)_2$ (R as defined above) |
| $Ca^{2+}$ | $Ga^{3+}$ | $Cl^-$, $SO_4^{2-}$, $NO_3^{2-}$, $CO_3^{2-}$, $HO^-$, $HOO^-$, $ClO^-$, $HCO_3^-$, $RCOO^-$, $R(COO^-)_2$ (R as defined above) |
| $Ca^{2+}$ | $Fe^{3+}$ | $Cl^-$, $SO_4^{2-}$, $NO_3^{2-}$, $CO_3^{2-}$, $HO^-$, $HOO^-$, $ClO^-$, $HCO_3^-$, $RCOO^-$, $R(COO^-)_2$ (R as defined above) |
| $Zn^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Ni^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Co^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |
| $Cu^{2+}$ | $Al^{3+}$ | $CO_3^{2-}$, $HO^-$, $HOO^-$, $ClO^-$, $HCO_3^-$, $RCOO^-$, $R(COO^-)_2$ (R as defined above) |

Preferably, $x=\frac{1}{3}$ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HO^-$, $HOO^-$, $ClO^-$, $HCO_3^-$ |
| $Mg^{2+}$ | $Al^{3+}$ | $CO_3^{2-}$, $HO^-$, $HOO^-$, $ClO^-$, $HCO_3^-$ |
| $Mg^{2+}$ | $Fe^{3+}$ | $CO_3^{2-}$, $HO^-$, $HOO^-$, $ClO^-$, $HCO_3^-$ |
| $Ca^{2+}$ | $Al^{3+}$ | $Cl^-$, $SO_4^{2-}$, $NO_3^{2-}$, $CO_3^{2-}$, $HO^-$, $HOO^-$, $ClO^-$, $HCO_3^-$ |
| $Ca^{2+}$ | $Ga^{3+}$ | $Cl^-$, $SO_4^{2-}$, $NO_3^{2-}$, $CO_3^{2-}$, $HO^-$, $HOO^-$, $ClO^-$, $HCO_3^-$ |
| $Ca^{2+}$ | $Fe^{3+}$ | $Cl^-$, $SO_4^{2-}$, $NO_3^{2-}$, $CO_3^{2-}$, $HO^-$, $HOO^-$, $ClO^-$, $HCO_3^-$ |
| $Zn^{2+}$ | $Al^{3+}$ | $CO_3^{2-}$, $HO^-$, $HOO^-$, $ClO^-$, $HCO_3^-$ |
| $Ni^{2+}$ | $Al^{3+}$ | $CO_3^{2-}$, $HO^-$, $HOO^-$, $ClO^-$, $HCO_3^-$ |
| $Co^{2+}$ | $Al^{3+}$ | $CO_3^{2-}$, $HO^-$, $HOO^-$, $ClO^-$, $HCO_3^-$ |
| $Cu^{2+}$ | $Al^{3+}$ | $CO_3^{2-}$, $HO^-$, $HOO^-$, $ClO^-$, $HCO_3^-$ |

Preferably, $x=\frac{1}{3}$ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HO^-$, $HOO^-$, $ClO^-$, $HCO_3^-$ |
| $Mg^{2+}$ | $Al^{3+}$ | $CO_3^{2-}$, $HO^-$, $HOO^-$, $ClO^-$, $HCO_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HO$^-$, HOO$^-$, ClO$^-$, HCO$_3^-$ |
| Mg$^{2+}$ | Al$^{3+}$ | CO$_3^{2-}$, HO$^-$, HOO$^-$, ClO$^-$, HCO$_3^-$ |
| Ca$^{2+}$ | Al$^{3+}$ | Cl$^-$, SO$_4^{2-}$, NO$_3^{2-}$, CO$_3^{2-}$, HO$^-$, HOO$^-$, ClO$^-$, HCO$_3^-$ |
| Zn$^{2+}$ | Al$^{3+}$ | CO$_3^{2-}$, HO$^-$, HOO$^-$, ClO$^-$, HCO$_3^-$ |
| Ni$^{2+}$ | Al$^{3+}$ | CO$_3^{2-}$, HO$^-$, HOO$^-$, ClO$^-$, HCO$_3^-$ |
| Co$^{2+}$ | Al$^{3+}$ | CO$_3^{2-}$, HO$^-$, HOO$^-$, ClO$^-$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Mg$^{2+}$ | Fe$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Ca$^{2+}$ | Ga$^{3+}$ | Cl$^-$, SO$_4^{2-}$, NO$_3^{2-}$, CO$_3^{2-}$, HCO$_3^-$ |
| Ca$^{2+}$ | Fe$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Ni$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |
| Cu$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Ca$^{2+}$ | Ga$^{3+}$ | Cl$^-$, SO$_4^{2-}$, NO$_3^{2-}$, CO$_3^{2-}$, HCO$_3^-$ |
| Ca$^{2+}$ | Fe$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Ni$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |
| Cu$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Mg$^{2+}$ | Fe$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Ni$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |
| Cu$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Ni$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |
| Cu$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Ni$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Mg$^{2+}$ | Fe$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |
| Cu$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |
| Cu$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| Li$^+$ | Al$^{3+}$ | CO$_3^{2-}$, HCO$_3^-$ |
| Mg$^{2+}$ | Al$^{3+}$ | CO$_3^{2-}$, HCO$_3^-$ |
| Ca$^{2+}$ | Al$^{3+}$ | Cl$^-$, SO$_4^{2-}$, NO$_3^{2-}$, CO$_3^{2-}$, HCO$_3^-$ |
| Zn$^{2+}$ | Al$^{3+}$ | CO$_3^{2-}$, HCO$_3^-$ |
| Ni$^{2+}$ | Al$^{3+}$ | CO$_3^{2-}$, HCO$_3^-$ |
| Co$^{2+}$ | Al$^{3+}$ | CO$_3^{2-}$, HCO$_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HCO_3^-$ |
| $Mg^{2+}$ | $Al^{3+}$ | $CO_3^{2-}$, $HCO_3^-$ |
| $Mg^{2+}$ | $Fe^{3+}$ | $CO_3^{2-}$, $HCO_3^-$ |
| $Ca^{2+}$ | $Al^{3+}$ | $Cl^-$, $SO_4^{2-}$, $NO_3^{2-}$, $CO_3^{2-}$, $HCO_3^-$ |
| $Ca^{2+}$ | $Fe^{3+}$ | $Cl^-$, $SO_4^{2-}$, $NO_3^{2-}$, $CO_3^{2-}$, $HCO_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HCO_3^-$ |
| $Mg^{2+}$ | $Al^{3+}$ | $CO_3^{2-}$, $HCO_3^-$ |
| $Mg^{2+}$ | $Fe^{3+}$ | $CO_3^{2-}$, $HCO_3^-$ |
| $Ca^{2+}$ | $Al^{3+}$ | $NO_3^{2-}$, $CO_3^{2-}$, $HCO_3^-$ |
| $Ca^{2+}$ | $Fe^{3+}$ | $NO_3^{2-}$, $CO_3^{2-}$, $HCO_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$, $HCO_3^-$ |
| $Mg^{2+}$ | $Al^{3+}$ | $CO_3^{2-}$, $HCO_3^-$ |
| $Ca^{2+}$ | $Al^{3+}$ | $Cl^-$, $SO_4^{2-}$, $NO_3^{2-}$, $CO_3^{2-}$, $HCO_3^-$ |

Preferably, x=⅓ if the LDH is of formula (II). Preferably, the LDH is of formula (I) or (II).

In one embodiment, the LDH of formula (I), (II), or (III) is selected from the following:

| $M^I$ or $M^{II}$ | $M^{III}$ | A |
|---|---|---|
| $Li^+$ | $Al^{3+}$ | $CO_3^{2-}$ or $HCO_3^-$ |
| $Mg^{2+}$ | $Al^{3+}$ | $CO_3^{2-}$ or $HCO_3^-$ |
| $Ca^{2+}$ | $Al^{3+}$ | $NO_3^{2-}$, $CO_3^{2-}$, $HCO_3^-$ |

Preferably, x=⅓ if the LDH is of formula (II). Preferably, the LDH is of formula (I) or (II).

Examples of LDH compounds that are preferred for use in the present invention include:

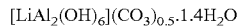

[LiAl$_2$(OH)$_6$](CO$_3$)$_{0.5}$·1.4H$_2$O

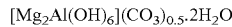

[Mg$_2$Al(OH)$_6$](CO$_3$)$_{0.5}$·2H$_2$O

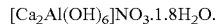

[Ca$_2$Al(OH)$_6$]NO$_3$·1.8H$_2$O.

The LDH compound [Mg$_2$Fe(OH)$_6$](CO$_3$)$_{0.5}$·2H$_2$O may also be preferred for use in the present invention.

The LDH compound [Ca$_2$Al(OH)$_6$]Cl·(H$_2$O)$_3$ may also be preferred for use in the present invention.

A Ca$_2$Al—CO$_3$ LDH may also be preferred for use in the present invention.

In one embodiment, the LDH compound is one in which none of the metal ions is redox-active (e.g. in one embodiment iron and copper ions are not present). There can be a preference to avoid the use of redox-active metal ions in some in vivo applications.

The LDH compound used in the present invention may have any suitable particle size. It may be that the particle diameter, as determined by electron microscopy, is from 100 nm to 750 nm, such as from 200 nm to 750 nm. A JEOL 2010 analytical transmission electron microscope, which has a LaB6 electron gun and can be operated between 80 and 200 kV, can be used for particle size determination. Additional information on particle size can be obtained from dynamic light scattering and disc centrifuge techniques.

In one embodiment, the particle diameter is from 200 nm to 600 nm, such as from 200 to 500 nm, or from 200 to 400 nm, or from 200 to 300 nm. LDHs with sizes in such ranges can give immunological effects, in terms of an effect on dendritic cell activation, an effect on T cell response and an effect on antibody induction.

In one embodiment of the invention, the LDH compound used in the present invention is a hybrid product that has biologically active agent and/or antigen intercalated therein. In such a hybrid LDH product some or all of the anion A is replaced by biologically active agent and/or antigen. For example, 10 wt % or more (such as 20 wt %, 30 wt %, 40 wt %, 50 wt %, 60 wt %, 70 wt %, 80 wt % or 90 wt % or more) of the anion A may be replaced by biologically active agent and/or antigen. In the event that any of the anion A is retained in the hybrid product it must meet the requirements for A as set out above.

A hybrid LDH may be formed by using anion exchange on a host material (e.g. [LiAl$_2$(OH)$_6$]Cl·H$_2$O, or [Ca$_2$Al(OH)$_6$]NO$_3$·H$_2$O). The host material should be chosen to ensure that, when taking into account the extent to which the biologically active agent and/or antigen will displace the anion A, the resultant hybrid meets the requirements of formula (I), (II) or (III).

The biologically active agent may be any agent that has a biological effect; for example it may be an agent that modulates an immune response.

Examples of the biologically active agent that may be intercalated are uric acid, ATP, AMP, GMP and cAMP.

Other biologically active agents that could potentially be intercalated include immune modulators selected from the group consisting of: metal salts, oil in water emulsions, Toll like receptor agonists, saponins, iscoms, polyethyleneimine or combinations thereof.

Any antigens, such as those mentioned below, may alternatively or additionally be intercalated.

The preparation of hybrid LDH compounds is known in the art, in particular via ion-exchange methods. For example, the production of hybrid LDH compounds with intercalated ATP, AMP, GMP and cyclic AMP (cAMP) is discussed in J. Mater. Chem., 2001, 11, 1671-1674 and Solid State Sciences, 2001, 3, 883-886.

In another embodiment, the LDH compound used in the present invention is not a hybrid product and therefore does not have any biologically active agent or antigen intercalated therein.

The LDHs and related compositions of the invention can be used for modulating immune responses to antigens (i.e. increasing immune responses to specific antigens, or preventing/inhibiting or otherwise reducing immune responses to specific antigens). They can be used for the prevention or treatment of: infectious diseases; allergies and other immune-related sensitivities (hypersensitivity diseases); autoimmune diseases; transplantation reactions (including transplant rejection and graft versus host disease); proliferative diseases including cancers; and other inflammatory conditions (including autoinflammatory conditions). They can be used for inducing tolerance, for immunotherapy or for immunosuppression.

When reference is made to modulating an immune response, the immune response may, for example, be selected from: a response to infectious diseases; a response due to allergies or other immune-related sensitivities (hypersensitivity diseases); a response due to autoimmune diseases; a response due to transplantation reactions (including transplant rejection and graft versus host disease); a response due to proliferative diseases including cancers; and a response due to other inflammatory conditions (including autoinflammatory conditions).

The conditions that may be treated or prevented in accordance with the present invention can generally be defined as infectious diseases; allergies and other immune-related sensitivities (hypersensitivity diseases); autoimmune diseases; transplantation reactions (including transplant rejection and graft versus host disease); proliferative diseases including cancers; and other inflammatory conditions (including autoinflammatory conditions).

Infectious diseases that may be mentioned include bacterial diseases and related conditions, such as tuberculosis, meningitis, tetanus, typhoid fever, diphtheria, syphilis, leprosy, typhus, pneumonia, salmonella, septicemia or septic shock; viral diseases, such as HIV, hepatitis, polio, yellow fever, dengue fever, measles, mumps, rubella, rabies, herpes, influenza or parainfluenza; parasitic diseases (caused by protozoa or metazoa), such as malaria, leishmaniasis, giardiasis or toxoplasmosis; and fungal infections, such as candidiasis, blastomycosis or histoplasmosis.

Allergies that may be mentioned include, but are not limited to, allergic reactions to pollens (e.g. birch tree, ragweed, oil seed rape), food (e.g. nuts, eggs or seafood), drugs (e.g. penicillin or salicylates), insect products (e.g. bee or wasp venom or house dust mites) or animal hair, and man-made products such as latex.

Immune-related sensitivities that can be mentioned include type I, (allergic) type II, type III, or type IV hypersensitivity disorders ('hypersensitivity reactions' according to the Gell-Coombs classification) and the less commonly defined type V hypersensitivity disorders. The disorders that can be mentioned include, but are not limited to, atopy, asthma, ertyhroblastosis fetalis, Goodpasture's syndrome, autoimmune hemolytic anemia, serum sickness, Arthus reaction, systemic lupus erythematosus, contact dermatitis, tuberculin skin test, chronic transplant rejection, Graves disease, myasthenia gravis, systemic anaphylaxis, local anaphylaxis, allergic rhinitis, conjunctivitis, gastroenteritis, eczema, blood transfusion reactions, haemolytic disease of the newborn, rheumatoid arthritis, glomerulonephritis, contact dermatitis, atopic dermatitis, tubercular lesions, drug-induced hemolytic anemia, lupus nephritis, aspergillosis, polyarteritis, polymyositis, scleroderma, hypersensitivity pneumonitis, Wegener's granulomastosis, type I diabetes mellitus, urticaria/angioedema, and inflammation of the thyroid.

Autoimmune disorders that may be mentioned include, but are not limited to, achlorhydra autoimmune active chronic hepatitis, Addison's disease, alopecia areata, amyotrophic lateral sclerosis (ALS, Lou Gehrig's Disease), ankylosing spondylitis, anti-GBM nephritis or anti-TBM nephritis, antiphospholipid syndrome, aplastic anemia, arthritis, asthma, atopic allergy, atopic dermatitis, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Balo disease, Behcet's disease, Berger's disease (IgA Nephropathy), bullous pemphigoid, cardiomyopathy, celiac disease, celiac sprue dermatitis, chronic fatigue immune deficiency syndrome (CFIDS), chronic fatigue immune dysfunction syndrome (CFIDS), chronic inflammatory demyelinating polyneuropathy, Churg Strauss syndrome, cicatricial pemphigoid, Cogan's syndrome, cold agglutunin disease, colitis, cranial arteritis, CREST syndrome, Crohn's disease, Cushing's syndrome, Dego's disease, dermatitis, dermatomyositis, dermatomyositis—juvenile, Devic's disease, type 1 diabetes, discoid lupus, Dowling-Dego's disease, Dressler's syndrome, eosinophilic fasciitis, epidermolysis bullosa acquisita, essential mixed cryoglobulinemia, Evan's syndrome, fibromyalgia, fibromyositis, fibrosing alveolitis, gastritis, giant cell artertis, glomerulonephritis, Goodpasture's disease, Grave's disease, Guillian-Barre syndrome, Hashimoto's thyroiditis, hemolytic anemia, Henoch-Schonlein purpura, hepatitis, Hughes syndrome, idiopathic adrenal atrophy, idiopathic pulmonary fibrosis, idiopathic thrombocytopenia purpura (ITP), IgA nephropathy, inflammatory demylinating polyneuropathy, insulin dependent diabetes (Type I), irritable bowel syndrome, juvenile arthritis, Kawasaki's disease, lichen planus, Lou Gehrig's disease, lupoid hepatitis, Lyme disease, Meniere's disease, mixed connective tissue disease, multiple myeloma, multiple sclerosis, myasthenia gravis, myositis, ocular cicatricial pemphigoid, osteoporosis, pars planitis, pemphigus vulgaris, pernicious anemia, polyarteritis nodosa, polychondritis, polyglancular syndromes, polyglandular autoimmune syndromes, polymyalgia rheumatica (PMR), polymyositis, polymyositis and dermatomyositis, primary agammaglobulinemia, primary biliary cirrhois, primary biliary cirrhosis, primary sclerosing cholangitis, psoriasis, Raynaud's phenomenon, Reiter's syndrome, rheumatoid arthritis, sarcoidosis, scleritis, scleroderma, Sjogren's syndrome, sticky blood syndrome, stiff-man syndrome, Still's disease, sydenham chorea, systemic lupus erythmatosis (SLE), Takayasu's arteritis, temporal arteritis/giant cell arteritis, ulcerative colitis, uveitis, vasculitis, vitiligo, Wegener's granulomatosis, and Wilson's syndrome.

The transplantation reactions may be reactions subsequent to isografts (between the same individual) or allografts (between different members of the same species) or xenografts (between different species). The reactions that may be mentioned include rejection of transplants including, but not limited to, heart transplant, lung transplant, heart and lung transplant, kidney transplant, liver transplant, pancreas transplant, intestine transplant, hand transplant, cornea transplant, skin graft (including face replant and face transplants), islets of Langerhans transplant, bone marrow transplant, blood transfusion, blood vessel transplant, heart valve transplant. The reactions that may be mentioned also include graft-versus host disease following bone marrow transplantation.

Cancers that may be mentioned include haematological cancers, such as lymphoma or leukaemia or multiple myeloma. Leukemias include, but are not limited to, acute lymphoblastic leukaemia (ALL), acute myelogenous leukaemia (AML), chronic myelogenous leukaemia (CML), chronic lymphocytic leukaemia (CLL) and hairy cell leukaemia. Lymphomas include but are not limited to Hodgkin's disease and non-Hodgkin's lymphoma. Cancers that may be mentioned also include carcinomas, sarcomas, and blastomas, and include, but are not limited to, cancers of the breast, lung, ovaries, pancreas, testes, skin, colon, brain, liver or cervix, as well as melanoma and histiocytoma. Other proliferative diseases include myelodysplastic syndrome (MDS) which can culminate in ALL, myeloproliferative disease, including polycythemia vera, essential thrombocytosis or myelofibrosis, and amyloid due to light-chain disease.

Inflammatory conditions that may be mentioned include, but are not limited to, acute respiratory distress syndrome and giant cell arteritis.

An antigen is a substance, in particular a molecule or molecular fragment, against which an adaptive immune response may be directed, which response may involve antibodies or cytotoxic T cells, or both.

The antigen may be an extrinsic antigen (e.g. a foreign non-infectious antigen) or an intrinsic antigen (e.g. an autoimmune antigen).

The antigen may be an antigen for use in DNA vaccination. Thus the antigen may be a macromolecule, such as a polypeptide chain, an RNA preparation that can be translated into a polypeptide chain, or a DNA preparation that encodes a polypeptide chain and that may be transcribed into an RNA intermediate. The antigen may, for example, be a DNA plasmid that has been genetically engineered to produce one or more specific polypeptide against which an adaptive immune response may be directed.

The antigen may be an autologous or syngeneic antigen, an allogeneic antigen, or a xenogeneic antigen. The antigen may be selected from virally-derived antigens; bacterially-derived antigens; fungal derived antigens (including yeast- and mould-derived antigens); protozoan parasite-derived antigens; metazoan parasite-derived antigens; tumour antigens; blood group antigens; allergens and substances triggering other immune related sensitivities; transplantation antigens; and self antigens.

The antigen may be an antigen of an infectious disease agent, and in this regard may be any viral, microbial, fungal or parasitic antigen. The antigen may be an antigen for allergies or other immune-related sensitivities (hypersensitivity diseases), and in this regard may be any extrinsic antigen, including an allergen or other immune sensitizer. The antigen may be an antigen for autoimmune disease, and in this regard may be any intrinsic or 'self' antigen. The antigen may be an antigen for transplantation reactions (including graft rejection and graft versus host disease) and in this regard may be any transplantation antigen. The antigen may be an antigen for proliferative diseases including cancers, and in this regard may be any tumour antigens, including oncogenic antigens or mutated, over-expressed or aberrantly-expressed 'self' antigens.

Specific examples of antigens that may be mentioned are: virally-derived antigens, bacterially-derived antigens, parasite-derived antigens, yeast- or other fungus-derived antigens and tumour antigens. These are all antigens where specific types of immune response to the antigen can desirably be increased.

Specific examples of other antigens that may be mentioned are: 'extrinsic' allergens, contact sensitisers and 'intrinsic' self antigens. These are all antigens where a specific type of immune response to the antigen can desirably be decreased.

In one embodiment, the antigen is virally derived from a virus that affects humans, e.g. HIV-1, hepatitis virus, parainfluenza, measles virus, mumps virus, human papilloma viruses, flaviviruses, orthomyxoviruses, paramyxoviruses, human herpes viruses, cytomegalovirus, Epstein Barr virus, Varicella Zoster virus, or Respiratory Syncytial virus.

In one embodiment, the antigen is virally derived from a virus that affects non-human animals, e.g. *M. bovis*, Foot and Mouth Disease virus, Bluetongue, Peste-des-petits-ruminants virus (PPR), *Salmonella* or *Pasteurella*.

In one embodiment, the antigen is derived from bacterial pathogens such as *Neisseria* spp; *Moraxella* spp; *Bordetella* spp; *Mycobacterium* spp; *Legionella* spp; *Escherichia* spp; *Vibrio* spp; *Shigella* spp; *Yersinia* spp; *Campylobacter* spp; *Salmonella* spp; *Listeria* spp; *Helicobacter* spp; *Pseudomonas* spp; *Staphylococcus* spp; *Enterococcus* spp.; *Clostridium* spp.; *Bacillus* spp.; *Corynebacterium* spp.; *Borrelia* spp.; *Ehrlichia* spp.; *Rickettsia* spp; *Chlamydia* spp.; *Leptospira* spp.; or *Treponema* spp.

In one embodiment, the antigen is derived from parasites, which may be protozoa (single-celled) or metazoa (multicellular, such as worms). Examples include *Plasmodium* spp.; *Toxoplasma* spp; *Entamoeba* spp.; *Babesia* spp.; *Trypanosoma* spp.; *Giardia* spp; *Leshmania* spp.; *Pneumocystis* spp.; *Trichomonas* spp; or *Schisostoma* spp.

In one embodiment, the antigen is derived from fungi, in particular yeast, such as *Candida* spp.; or *Cryptococcus* spp.

In one embodiment, the antigen is a tumour antigen which results in a proliferative disease such as prostate, breast, colorectal, lung, pancreatic, renal, ovarian or melanoma cancer. These include oncogenic antigens or mutated, over-expressed or aberrantly-expressed 'self' antigens.

In one embodiment, the antigen is an allergen, for example allergens selected from animal parasites, insect venoms, house mites, chemical allergens, bacterial allergens, viral allergens, dust, medicaments such as antibiotics, foods such as nuts, fish or dairy products, perfumes, plants, pollen, and smoke.

In one embodiment, the antigen is a self antigen, for example insulin, glutamic acid decarboxylase, heat shock protein, myelin oligodendrocyte glycoprotein (MOG), myelin antigens (MBP and PLP), zona pellucida 3 (ZP3), myoglobulin, type II collagen, thyroglobulin, cell membrane surface antigen, type II colloid antigen (CA2), acetylcholine receptor, thyrocyte cell surface antigen (TSH), salivary gland duct antigen, thyroglobulin, superantigen (S—Ag), or interphotoreceptor retinoid binding protein.

As will be appreciated by the skilled reader, the amount of antigen in each dose is selected as an amount which induces an immune response without significant adverse side effects in typical experimental animals or subjects being treated. Generally, it is expected that each dose will comprise from 1 µg/kg to 1 g/kg of antigen, preferably 1 µg/kg to 0.5 g/kg, more preferably 10 µg/kg to 0.1 g/kg, most preferably 10 µg/kg to 0.05 g/kg. An optimal amount can be ascertained by standard studies involving observation of appropriate immune responses in treated subjects or experimental animals.

Equally, the amount of LDH in each dose is selected as an amount which modulates an immune response without significant adverse side effects in typical subjects being treated. Generally, it is expected that each dose will comprise from 1 µg/kg to 1 g/kg of LDH, preferably 10 µg/kg to 500 mg/kg, more preferably 100 µg/kg to 100 mg/kg, most preferably 1 mg/kg to 50 mg/kg. An optimal amount can be ascertained by standard studies involving observation of appropriate immune responses in treated subjects or experimental animals.

Following an initial dose, subjects may receive one or several booster doses adequately spaced. Therefore the compositions of the invention may be applied to a subject in a priming and/or a boosting regime.

Such a regime may be administered systemically, for example via the transdermal, subcutaneous, intramuscular, intravenous, or intradermal routes; mucosally by the oral, rectal, vaginal, intranasal, or deep lung route (e.g. using an inhaler); or topically.

In one embodiment, the composition or medicament of the invention may additionally comprise one or more pharmaceutically acceptable excipients. The pharmaceutically acceptable excipients may be carriers, diluents, binders, lubricants, preservatives, stabilizers, dyes, antioxidants, suspending agents, coating agents, solubilising agents and/or flavouring agents.

Examples of suitable carriers include lactose, starch, glucose, methyl cellulose, magnesium stearate, mannitol, sorbitol and the like. Examples of suitable diluents include ethanol, glycerol, water and the like. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Examples of suitable preservatives include sodium benzoate, sorbic acid and esters of p-hydroxybenzoic acid and the like.

In one embodiment, the LDH may be provided with, or administered with, one or more biologically active agent. The biologically active agent and the LDH (or composition or medicament comprising the LDH) may be administered simultaneously, may be administered simultaneously, sequentially (in either order) or separately (in either order). When administered separately there may be a time delay between administering the two components of, for example, 15 minutes or more, such as 30 minutes or more. Preferably they are administered simultaneously or sequentially.

The compositions, kits and medicaments of the invention as described above may therefore optionally further comprise one or more biologically active agent. Equally, the compositions and medicaments of the invention as described above may be provided for administration with a biologically active agent, simultaneously, (in either order) or separately (in either order). When administered separately there may be a time delay between administering the components of, for example, 15 minutes or more, such as 30 minutes or more. Preferably they are administered simultaneously or sequentially.

The biologically active agent may be any agent that has a biological effect—for example it may be an agent that modulates an immune response.

The one or more biologically active agent may, in one embodiment, be selected from the group consisting of: uric acid, ATP, AMP, GMP and cAMP, metal salts, oil in water emulsions, Toll like receptor agonists, saponins, iscoms, polyethyleneimine or combinations thereof.

The composition of the invention may be provided in any suitable form for delivery. Conventional pharmaceutical delivery systems may be used in this regard, such as polymer matrices, enteric coatings, biolistic (gene) gun delivery systems or nanopatches.

The animals that may be the subject of the increased or a decreased immune response, and that may be treated using the products and methods of the invention, include humans, non-human mammals, birds and fish. The animals include farm animals such as cows, horses, sheep, pigs, chickens, geese and ducks; and domestic pets such as cats, dogs and rabbits. The animal may also be selected from experimental animals, such as rodents, in particular mice and rats.

The invention will now be further described with reference to the following non-limiting examples.

EXAMPLES

1. LDH Production—Materials, Synthesis and Characterisation

The hexagonal polymorph of $[LiAl_2(OH)_6]Cl.yH_2O$ (hereafter $LiAl_2$—Cl) was synthesised by suspending 1 g of γ-Al (OH)$_3$ (gibbsite) in 20 mL of a 15M solution of LiCl. The suspension was stirred at 90° C. for ca. 15 h in a sealed ampoule. The solid product was recovered by vacuum filtration, washed with copious amounts of deionised water and acetone, and dried under vacuum for ca. 3 hours.

The hexagonal polymorph of $[LiAl_2(OH)_6]_2CO_3.yH_2O$ (hereafter $LiAl_2$—$CO_3$) was produced by reacting 0.216 g of h-$LiAl_2$—Cl with a 6-fold excess of $Li_2CO_3$ in 12.5 mL deionised water for ca. 15 hours at room temperature. The solid product was recovered by vacuum filtration, washed with copious amounts of deionised water and acetone, and dried under vacuum for ca. 3 hours.

$[Mg_2Al(OH)_6]NO_3.yH_2O$ (hereafter $Mg_2Al$—$NO_3$) was formed by a co-precipitation approach. Two solutions (A and B) were prepared, and solution A was added slowly to solution B over a period of 2-4 h. Solution A contained 20.5 g of $Mg(NO_3)_2.6H_2O$ and 15 g of $Al(NO_3)_3.9H_2O$ dissolved in 100 mL of deionised water. Solution B was prepared by dissolving 6.7 g of NaOH and 9.5 g of NaNO3 in 100 mL of deionised water. Once addition was completed, the reaction gel was stirred at 75° C. for 24 h. The solid product was recovered by vacuum filtration, washed with copious amounts of deionised water and acetone, and dried under vacuum for ca. 3 hours.

$[Mg_2Al(OH)_6]_2CO_3.yH_2O$ (hereafter $Mg_2Al$—$CO_3$) was synthesised by reacting 0.551 g $Mg_2Al$—$NO_3$ with 1.06 g $Na_2CO_3$ in 25 mL deionised water for approximately 15 hours. The solid product was recovered by vacuum filtration, washed with copious amounts of deionised water and acetone, and dried under vacuum for ca. 3 hours.

$[Mg_2Fe(OH)_6]Cl.H_2O$ (hereafter $Mg_2Fe$—Cl) was produced by an analogous co-precipitation process to that used to create $Mg_2Al$—$NO_3$. In this case, solution A contained 7.50 g of $FeCl_3.6H_2O$ and 16.70 g of $MgCl_2.6H_2O$ in 100 mL deionised water and solution B contained 6.69 g of NaOH and 6.47 g of $Na_2CO_3$ in 100 mL deionised water. Addition of solution A to solution B was undertaken over ca. 2-4 h, and the resultant reaction gel was stirred at 75° C. for 24 h. The solid product was recovered by vacuum filtration, washed with copious amounts of deionised water and acetone, and dried under vacuum for ca. 3 hours.

$[Ca_2Al(OH)_6]NO_3.yH_2O$ (hereafter $Ca_2Al$—$NO_3$) was produced by an analogous co-precipitation process to that used to create $Mg_2Al$—$NO_3$. Solution A contained 19.59 g of $Ca(NO_3)_2.4H_2O$ and 10.37 g of $Al(NO_3)_3.9H_2O$ in 100 mL deionised water and solution B was 6.64 g NaOH and 9.4 g of $NaNO_3$ in 100 mL deionised water. Addition of solution A to solution B was undertaken over ca. 2-4 h, and the resultant reaction gel was stirred at 75° C. for 24 h. The solid product was recovered by vacuum filtration, washed with copious amounts of deionised water and acetone, and dried under vacuum for ca. 3 hours.

$[Mg_2Fe(OH)_6](CO_3)_{0.5}.yH_2O$ ($Mg_2Fe$—$CO_3$) was synthesised through the reaction of 0.25 g of $[Mg_2Fe(OH)_6]$ $Cl.yH_2O$ with a 5-fold excess of $Na_2CO_3$ at room temperature for ca. 15 h. The solid product was recovered by vacuum filtration, washed with copious amounts of water and acetone, and dried under vacuum for ca. 3 hours.

All the LDHs were fully characterised using X-ray diffraction, thermogravimetric analysis, elemental microanalysis, transmission electron microscopy, dynamic light scattering, and disc centrifugation.

1.1. Elemental Microanalysis of LDHs

C, H, and N were analysed. The samples were quantitatively digested through oxidative combustion to determine the content of each element. The results, together with formulae calculated from them, are detailed in Table 1.1.

TABLE 1.1

Elemental analysis of LDHs

| Compound | Formula | C % Calcd | C % Obsd | H % Calcd | H % Obsd | N % Calcd | N % Obsd |
|---|---|---|---|---|---|---|---|
| $LiAl_2$—Cl | $[LiAl_2(OH)_6]Cl \cdot H_2O$ | 0 | <0.1 | 3.97 | 3.62 | 0 | <0.1 |
| $LiAl_2$—$CO_3$ | $[LiAl_2(OH)_6](CO_3)_{0.5} \cdot 1.4H_2O$ | 2.75 | 2.78 | 4.06 | 3.9 | 0 | <0.1 |
| $Mg_2Al$—$NO_3$ | $[Mg_2Al(OH)_6]NO_3 \cdot 1.6H_2O$ | 0 | <0.1 | 3.45 | 3.29 | 5.21 | 5.53 |
| $Mg_2Al$—$CO_3$ | $[Mg_2Al(OH)_6](CO_3)_{0.5} \cdot 2H_2O$ | 2.46 | 2.54 | 4.13 | 3.65 | 0 | <0.1 |
| $Mg_2Fe$—Cl | $[Mg_2Fe(OH)_6]Cl \cdot H_2O$ | 0 | <0.1 | 3.11 | 2.78 | 0 | <0.1 |
| $Ca_2Al$—$NO_3$ | $[Ca_2Al(OH)_6]NO_3 \cdot 1.8H_2O$ | 0 | <0.1 | 3.18 | 2.83 | 4.62 | 4.75 |
| $Mg_2Fe$—$CO_3$ | $[Mg_2Fe(OH)_6](CO_3)_{0.5} \cdot 2H_2O$ | 2.36 | 2.46 | 3.17 | 3.25 | 0 | 0 |

1.2 Physicochemical Properties of LDHs

Standard electrode potentials and surface pKa values of compounds were obtained from published references where available. These are shown below in Table 1.2.

TABLE 1.2

Physicochemical properties of LDH compounds

| Property | $LiAl_2$—Cl | $LiAl_2$—$CO_3$ | $Mg_2Al$—$NO_3$ | $Mg_2Al$—$CO_3$ | $Mg_2Fe$—Cl | $Mg_2Fe$—$CO_3$ | $Ca_2Al$—$NO_3$ |
|---|---|---|---|---|---|---|---|
| Standard electrode potential $M^+/M^{2+} \to M^0$ | −3.04 V | −3.04 V | −2.37 V | −2.37 V | −2.37 V | −2.37 V | −2.87 V |
| Standard electrode potential $M^{3+} \to M^0$ | −1.66 V | −1.66 V | −1.66 V | −1.66 V | −0.037 V | −0.037 V | −1.66 V |
| Surface pKa | <4.2 | >12.2 | <4.8 | >12.2 | 3.2-6.2 | 11.9-13.8 | 12-14.5 |

1.3. Particle Size Analysis of LDHs

Particle size analysis was performed on a JEOL 2010 analytical transmission electron microscope, which has a $LaB_6$ electron gun and can be operated between 80 and 200 kV. This instrument has a resolution of 0.19 nm, an electron probe size down to 0.5 nm and a maximum specimen tilt of ±10 degrees along both axes. The instrument is equipped with an Oxford Instruments LZ5 windowless energy dispersive X-ray spectrometer (EDS) controlled by INCA. It has facilities for point analysis as well as mapping and line scanning through the SemiStem controller.

Additional experiments were performed using dynamic light scattering (DLS) and disk centrifuge (CPS) to determine sample size distributions. A summary of the findings is below in Table 1.3.

TABLE 1.3

Particle size distributions of LDH compounds

| Compound | Particle sizes (nm) TEM | DLS | CPS |
|---|---|---|---|
| $LiAl_2$—Cl | Particles from <100 nm to several micron in size. | Polydisperse distribution with particle sizes from approx 250-300 nm to several microns. | Very broad distribution with no distinguished peaks. |
| $LiAl_2$—$CO_3$ | Particles at approx 50-100 nm and aggregates from approx 100 nm to micron size. | Polydisperse distribution with peaks ranging from approx 300 nm to approx 2 micron. | Very broad distribution with no distinguished peaks. |
| $Mg_2Al$—$NO_3$ | Aggregates of a small number of particles appear at a size of approx 30 to 200 nm. In addition there are a few agglomerates of several hundreds of nm. | Narrow size distribution of approx 100 ± 10 nm. | Broad size distribution from about 20 to 250 nm. |
| $Mg_2Al$—$CO_3$ | Particles of approx 100-200 nm size, frequently embedded in debris. | Main peak at approx 120 nm plus some additional scattering from a small number of larger particles at approx 360 nm and 1.5 to 5.5 microns. | Measurement was not successful for this sample. |
| $Mg_2Fe$—Cl | A few small particles at approx 50-100 nm size, and a larger number of aggregates of around 200-500 nm size. | Main peak at approx 145 nm with a small number of particles in the 600-800 nm range. | One main peak at approx 70 ± 30 nm. |
| $Ca_2Al$—$NO_3$ | A few small aggregates of <100 nm size, and a larger number of micron-sized aggregates of thin single crystals. | Polydisperse sample with several peaks ranging from approx. 700 nm to 3 micron. | Very broad distribution with no distinguished peaks. |
| $Mg_2Fe$—$CO_3$ | N/A | Around 180 nm (estimated using the Scherrer equation | N/A |

2. In Vitro Testing on Human Dendritic Cells

Cell culture media and supplements were, unless otherwise stated, procured from PAA. This includes foetal calf serum (FCS), of which batches #A0430-0511 and A10107-1087 was employed throughout. LPS was obtained from Sigma (#4005).

Human monocyte-derived dendritic cells (moDC) were generated from peripheral blood monocytes (PBMC) isolated from healthy adult donors. Briefly, Buffy coats or leukocyte cones (National Blood Service) were mixed with at least an equal volume of $Ca^{2+}/Mg^{2+}$-free phosphate-buffered saline (PBS), carefully layered on to Lymphoprep (Axis Shield) and centrifuged at ~800 g for 30 minutes (at 22° C.). The peripheral blood mononuclear cell (PBMC) layer formed at the interface between the HBSS/Buffy coat mixture and Lymphoprep was carefully collected and washed three times with HBSS to remove platelets. Monocytes were isolated from PBMC by negative selection with magnetic beads.

For isolation of monocytes by negative selection (in other words, by the removal of non-monocytes), the PBMC pellets were resuspended in $Ca^{2+}/Mg^{2+}$-free HBSS, and monocytes were then isolated using the Dynal Monocyte Negative Isolation kit (Invitrogen), in accordance with the manufacturer's instructions. Purified monocytes were resuspended at $5 \times 10^5$/ml in DC-RPMI. (DC-RPMI is RPMI 1640 supplemented with 10% FCS, 2 mM L-glutamine, 100 U/ml penicillin, 100 µg/ml streptomycin, 1000 U/ml human GM-CSF and 500 U/ml human IL-4 (the latter two both from Gentaur)).

After 3 days, one third of the media was removed and spun down. The resultant pellet of cells was resuspended in the same volume of fresh media containing 3000 U/ml of GM-CSF, and 1500 U/ml of IL-4, then returned to the culture.

Normally, cells were used immediately after 6 days' culture. These cells will subsequently be referred to as 'fresh moDC'. But in some cases cells were frozen and thawed before use. Prior to freezing, they were washed with HBSS/2% FCS, resuspended in 5.5% hetastarch ("Voluven" from John Radcliffe Hospital pharmacy)/4.8% DMSO (Hybrimax grade from Sigma)/3.8% FCS in isotonic saline, then placed in a controlled freezing device (1 degree/minute) at −80° C. These cells will subsequently be referred to as 'frozen moDC'.

LDHs were synthesised as described above. Inject alum was procured from Fisher Scientific, and alhydrogel from Aldrich. The materials were adjusted from their supplied concentrations (40 mg/ml and 13 mg/ml respectively) to 10 mg/ml by dilution with PBS. Tests were carried out using inject alum, alhydrogel and the synthesised LDHs as test compounds.

For experiments to determine the influence of the test compounds on moDC, either fresh or frozen moDC were re-suspended at $5 \times 10^5$ cells per ml in DC-RPMI. A 96-well flat bottomed tissue culture plate (Corning) was prepared with 200 µl of moDC suspension in each well. LDH stocks were prepared by suspending each LDH in PBS at 10 mg/ml. Cells were pulsed with LPS at 100 ng/ml (by adding 1 µl of a 20,000 ng/ml LPS solution in PBS to a well), or with test compound at 500 µg/ml (by adding 10 µl of the test compound stocks to a well).

Assays to measure TNF-α production were undertaken using ELISA kits provided by Insight Biotechnology, in accordance with the manufacturer's instructions. Nunc absorbent ELISA plates were procured from VWR, and measurements recorded on an Athnos Lucy One 96-well microplate photospectrometer instrument at 405 nm.

Flow cytometric assays were used to quantify CD86 expression and cell death rate of DC exposed to test compounds. Flow cytometry was performed using a FACSort or FACSCanto flow cytometer (Becton Dickinson); data analysis was performed with CellQuest Pro and WinMDI 2.9, or with FACS Diva and FlowJo, respectively. Flow cytometry data are not presented but are summarised as part of the global assessment in Table 4A below.

2.1. TNF-α Secretion by Human Dendritic Cells—Effect of LDH

Fresh day 6 moDC were cultured untreated, pulsed with LPS at 100 ng/ml, or pulsed with test compound at 500 µg/ml. Supernatants were collected at 18 hours and analysed for TNF-α. FIG. 1 shows the concentration of TNF-α in the supernatant collected after treatment with each compound. The data are from a single experiment with measurements taken in quadruplicate. Each bar represents the mean TNF-α concentration from the four measurements, and the error bars depict the standard error of the mean.

It can be seen that $LiAl_2$—Cl, $LiAl_2$—$CO_3$ and $Mg_2Al$—$CO_3$ cause significant increased TNF-α secretion by human dendritic cells.

2.2. TNF-α Secretion by Human Dendritic Cells—Effect of Dose

Figure 2:
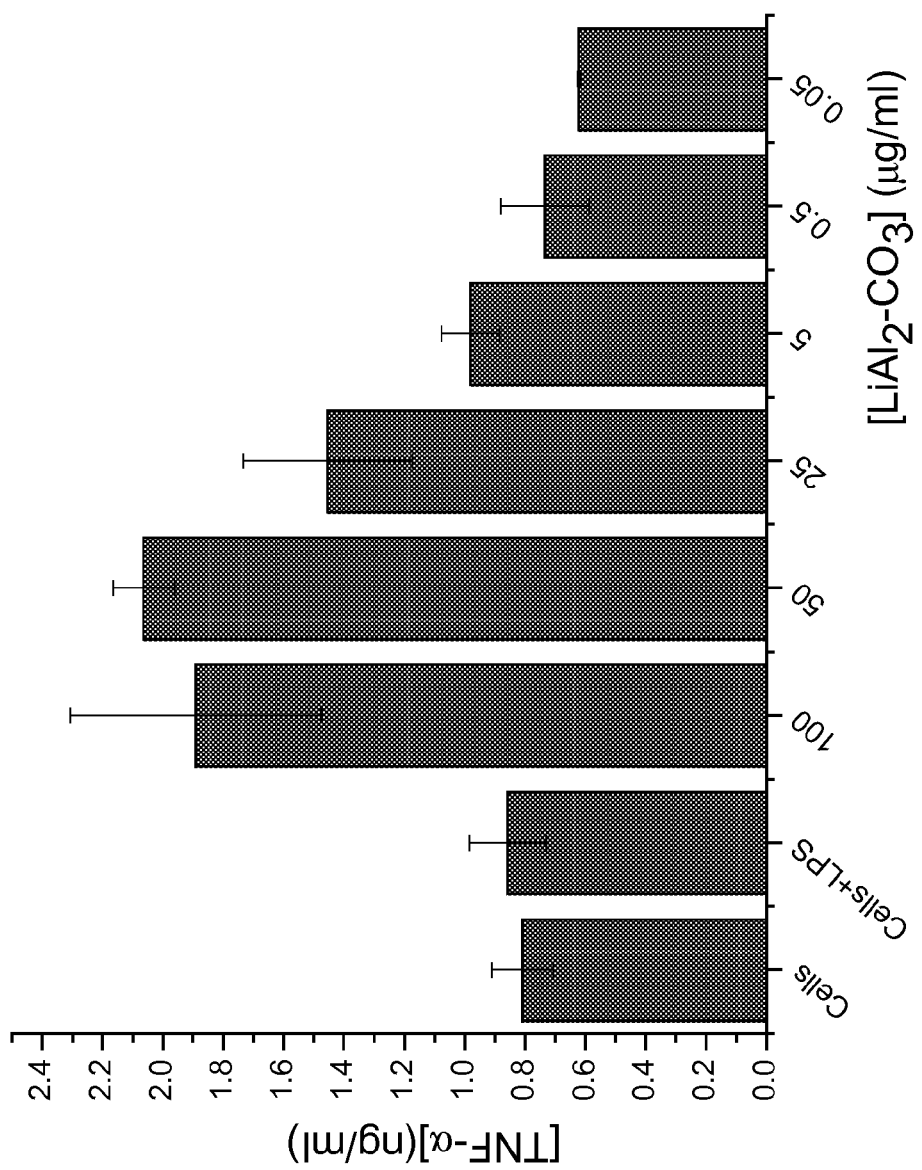

Fresh day 6 moDC were cultured untreated, pulsed with LPS at 100 ng/ml, or pulsed with $LiAl_2$—$CO_3$ at 1000, 500, 250, 50, 5 and 0.5 µg/ml. Supernatants were collected at 18 hours and analysed for TNF-α. FIG. 2 shows the concentration of TNF-α in the supernatant collected after treatment with each compound. The data are from a single experiment with measurements taken in quadruplicate. Each bar represents the mean TNF-α concentration from the four measurements, and the error bars depict the standard error of the mean.

It can be seen that an increased dose generally leads to an increased effect, up to a dose 500 µg/ml.

2.3. TNF-α Secretion by Human Dendritic Cells—Effect of LDH Plus LPS

Figure 3:
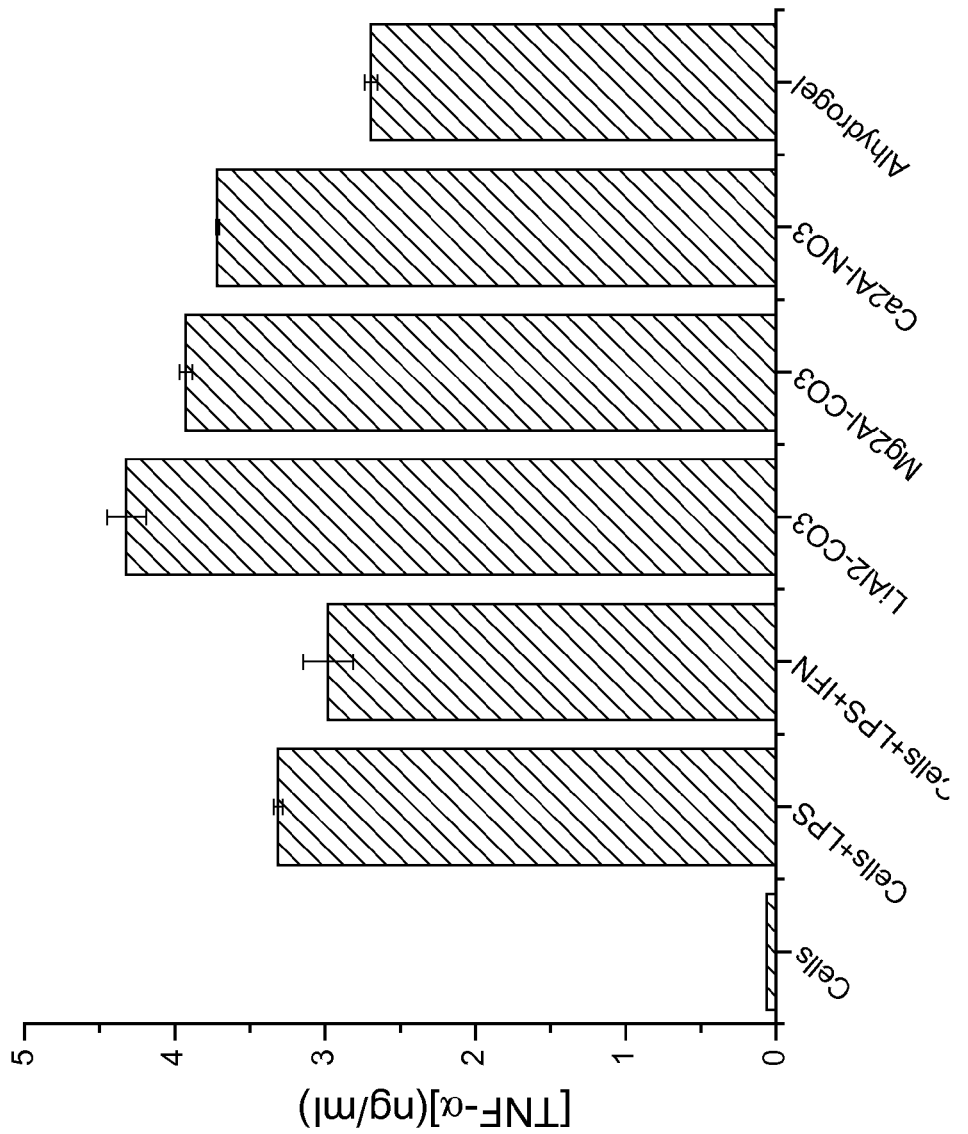

Frozen day 6 moDC were defrosted and cultured either untreated or with 10 ng/ml LPS. After 19 hours, some of the LPS-pulsed cells were additionally pulsed with IFN-γ at 20 ng/ml or test compound at 500 µg/ml. Supernatants were collected after another 22 hours and analysed for TNF-α. FIG. 3 shows the concentration of TNF-α in the supernatant collected. The data are from a single experiment with measurements taken in triplicate. Each bar represents the mean TNF-α concentration from the three measurements, and the error bars depict the standard error of the mean.

It can be seen that treatment of human dendritic cells with LPS and any of $LiAl_2$—$CO_3$, $Mg_2Al$—$CO_3$, or $Ca_2Al$—$NO_3$ causes increased TNF-α secretion compared to cells treated with LPS alone.

2.4 CD86 Secretion by Human Dendritic Cells—Effect of Dose

Figure 4:
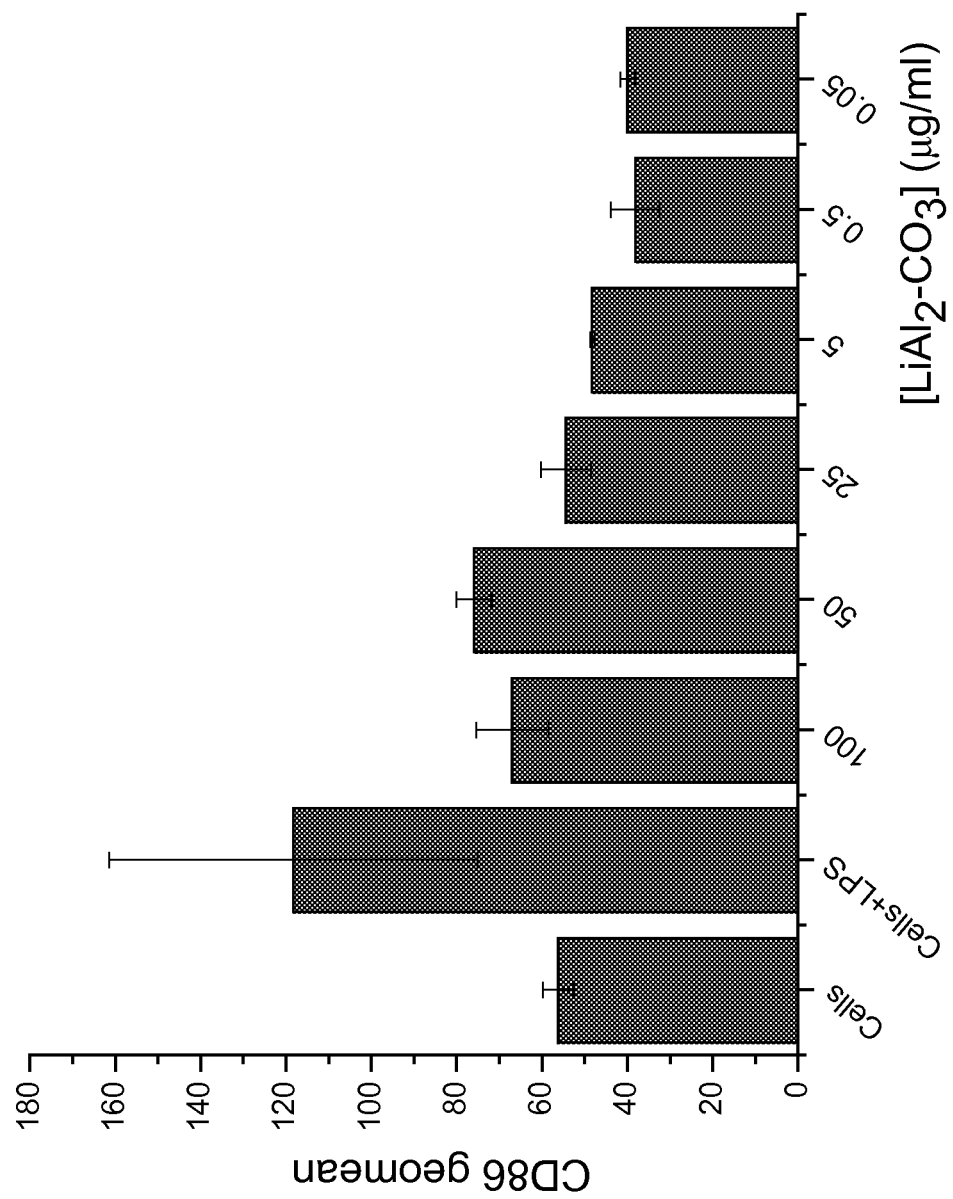

Fresh day 6 moDC were cultured untreated, pulsed with LPS at 100 ng/ml, or pulsed with $LiAl_2$—$CO_3$ at 1000, 500, 250, 50, 5 and 0.5 µg/ml. Cells were cultured for 18 hours before being stained with anti-CD86 antibody and analysed by flow cytometry. FIG. 4 shows the geometric mean of the CD86 expression of the cells after treatment with each compound. The data are from a single experiment with measurements taken in quadruplicate. Each bar represents the mean CD86 expression from the four measurements, and the error bars depict the standard error of the mean.

2.5. LDH Effect on Cell Death Rate

Frozen moDC were thawed, and cultured in 96-well flat-bottomed plates in DC-RPMI for 24 h. Subsequently, cells were left untreated, pulsed with LPS at 100 ng/ml, or pulsed with test compound at 500 µg/ml. After 25 h, the contents of each well were split into two. Cells were recovered by centrifugation and washed twice with HBSS/FCS. 10 µl of a $5\times10^6$ beads/ml microbead solution was added to the first sample from each well, and both cells and beads were counted by flow cytometery. The beads:cells ratio from flow cytometry was used to determine the number of cells in each well after pulsing and recovery.

Figure 5:
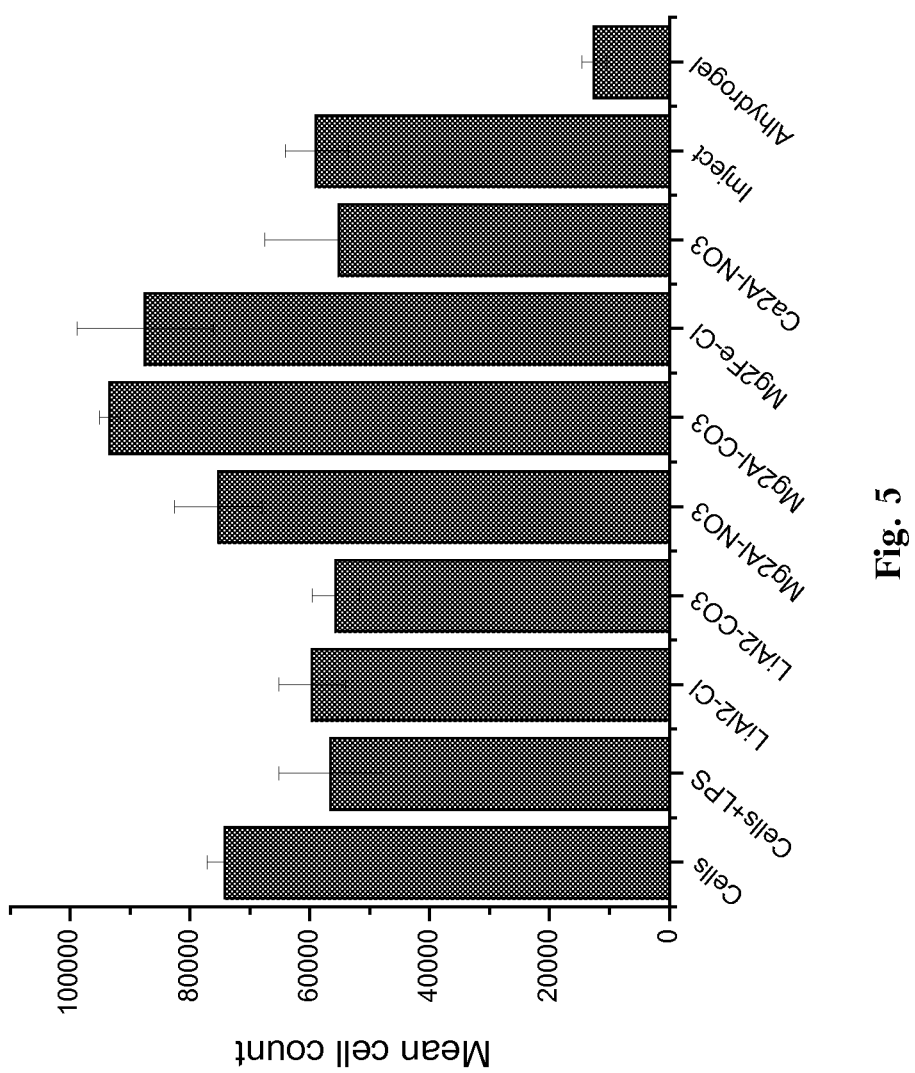

FIG. 5 shows data from a single experiment with measurements taken in triplicate. Each bar represents the mean cell count per well from the three measurements, and the error bars depict the standard error of the mean. There were approximately $10^5$ cells per well at the beginning of the experiment.

It can be seen that while a significant number of cells were lost in the process of analysis (during centrifugation etc), there is no substantial reduction in cell count for cells pulsed with test compound cf. unpulsed cells or cells pulsed with LPS, except in the case of alhydrogel.

3. In Vitro and In Vivo Testing on Mice

3.1. General Immunological Materials and Methods

Materials for In Vitro Testing of Mouse Bone Marrow Dendritic Cells

Bone marrow cells were cultured for a total of 9 days in DC culture medium (DC-CM; RPMI 1640 containing glutamax-I (Invitrogen, Carlsbad, Calif.) supplemented with 5% (v/v) FCS (Sigma-Aldrich), 50 µM 2-Mercaptoethanol (Sigma-Aldrich), 50 µg/ml gentamicin (Invitrogen), and 20 ng/ml recombinant mouse GM-CSF. On day 0 the bone marrow cells were re-suspended at $3\times10^6$ cells/ml in DC culture medium in Petri dishes (10 ml/plate). After 3 days, 10 ml fresh DC culture medium supplemented with 20 ng/ml GM-CSF was added to the cell cultures (final volume in each plate is 20 ml). On day 6, half of the media was removed and spun down. The resulting pellet of cells was re-suspended in the same volume of fresh medium containing 20 ng/ml GM-CSF and then returned to the cell culture. This procedure was repeated on day 8, 16 hr before harvesting, DCs were exposed either to OVA, Alum Inject/AlOH/LDH nanoparticles or OVA and Alum Inject/AlOH/LDHs (the concentration of OVA is always 100 µg/ml, Alum Inject/AlOH or the LDH nanoparticles are used at 480 µg/ml).

Ovalbumin (OVA) was purchased from Worthington Biochemical Corp (Lakewood, N.J.). Alum Inject is a mixture of aluminum hydroxide and magnesium hydroxide and is procured from Pierce Biochemicals. Alhydrogel was purchased from Sigma-Aldrich.

Materials for In Vivo Testing

Ovalbumin (OVA) was purchased from Worthington Biochemical Corp (Lakewood, N.J.). Inject alum was purchased from Pierce Biochemicals and is a mixture of aluminum hydroxide and magnesium hydroxide. Alhydrogel ('AlOH') was procured from Sigma-Aldrich. LDHs were synthesized as described above. The materials were adjusted to a concentration of 40 mg/ml in PBS. The Imject alum, AlOH or the LDHs were mixed at a 1:20 ratio with a solution of OVA antigen in saline followed by stirring for at least 1 h. For immunization 500 µl of the suspensions (1 mg) containing 10 µg of OVA (OVA-alum) was injected intraperitoneal (i.p.) in the right lower quadrant using a 26 G needle, alternatively 10 µg of OVA in 500 µl saline or saline alone was injected.

3.2. Flow Cytometry of DCs

To look at the activation profile of DCs in the culture, flow cytometry was used. PerCp Cy5.5-labeled MHCII and APC-labeled CD11c/PE-Texas Red labeled CD11c were used to gate the DCs. To avoid nonspecific binding cells were incubated with 2.4G2 Fc Receptor blocking Ab. To exclude dead cells from the staining, 7AAD or DAPI was added. The DCs were phenotyped by PE-labeled CD40, CD80, PD-L1, iCOSL, PE-Cy7 labeled CD86, Fitc-labeled PD-L2 or isotype controls.

Specifically, the DCs were phenotyped by PE-labeled CD80 or ICOS-L, APC-labeled CD40 or PD-L1, PE-Cy7 labeled CD86, FITC-labeled PD-L2, or respective isotype controls.

Flow cytometry was performed using a FACS Aria II or a FACS LSR II flow cytometer (Becton Dickinson) controlled using FacsDiva. Data analysis was performed with FlowJo version 8.8.6.

Data are not presented but are summarised as part of the global assessment of 'DC activation in vitro' in Table 4B below.

3.3. Antigen Presentation to T Cells In Vitro

OVA-specific TCR Tg CD8' T cells (OT-I) or CD4+ T cells (OT-II) were isolated from spleen and lymph nodes either purified $CD8^+$ or $CD4^+$ T cells respectively, using MACS (Miltenyi Biotec) or not purified. Tcells (purified or not) are labeled with CFSE (Invitrogen). Cells were resuspended in PBS or medium without serum, warmed up to 37° C. in a water bath and 10 µl of CFSE (0.5 mM) per ml of cell suspension was added. Cells were incubated for 10 min at 37° C. while inversed every 2 minutes. An excess of warm culturing medium was added to block the reaction. Cells were washed twice with culturing medium supplemented with FCS.

$4*10^4/2*10^4/1*10^4$ DCs (ratio 1:5/1:10/1:20) were cultured with $2*10^5$ $CD8^+$ or $CD4^+$ purified T cells or unpurified T cells in 96 well round bottom plates at 37° C. for 96 hrs. After 4 days, supernatant of the cells was collected and frozen at −20° C. for further analysis in ELISA. Cells were harvested and OVA-specific T cell proliferation was determined by staining CFSE labeled OT-I or OT-II cells with anti-Vβ5 PE (BD Bioscience) and anti-Vα2 biotin with streptavidine APC-Cy7.

The results are summarised as part of the global assessment of 'T cell in vitro' in Table 4B below.

3.4. Cytokine Secretion by Mouse Dendritic Cells—Effect of LDH

Mouse bone marrow cell suspensions were cultured for a total of 9 days in DC culture medium (DC-CM; RPMI 1640 containing glutamax-I (Invitrogen, Carlsbad, Calif.) supplemented with 5% (v/v) FCS (Sigma-Aldrich), 50 µM 2-Mercaptoethanol (Sigma-Aldrich), 50 µg/ml gentamicin (Invitrogen), and 20 ng/ml recombinant mouse GM-CSF. On day 0 the bone marrow cells were re-suspended at $3\times10^5$ cells/ml in DC culture medium in Petri dishes (10 ml/plate). After 3 days, 10 ml fresh DC culture medium supplemented with 20 ng/ml GM-CSF was added to the cell cultures. On day 6, half of the media was refreshed. 16 hrs before harvesting, DCs were cultured with or without Alum Imject (Imject), Alhydrogel (AlOH) or LDH nanoparticles, in the presence or absence of ovalbumin (OVA). Imject, a mixture of aluminum hydroxide and magnesium hydroxide, was procured from Pierce Biochemicals, AlOH was purchased from Sigma-Aldrich, and OVA was purchased from Worthington Biochemical Corp (Lakewood, N.J.). Imject, AlOH and LDH nanoparticles were used at 480 µg/ml and OVA at 100 µg/ml. After treatment, cells were harvested and cell supernatants were collected and frozen at −20° C. until analysis. Using ELISA, the amount of IL-1β, TNF-α, and IL-10 (eBioscience) was then measured in the supernatants.

Figure 6A:
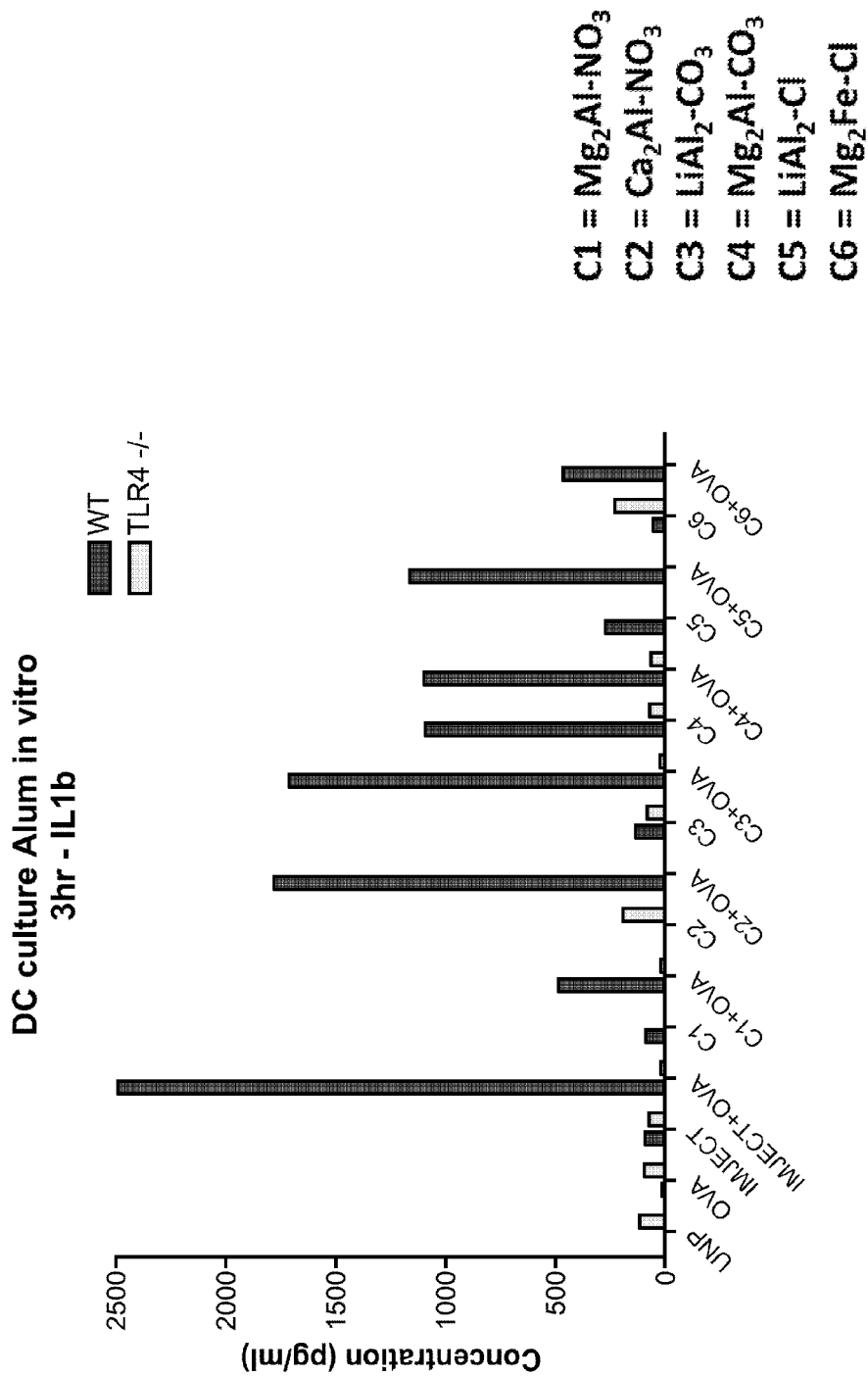
Figure 6B:
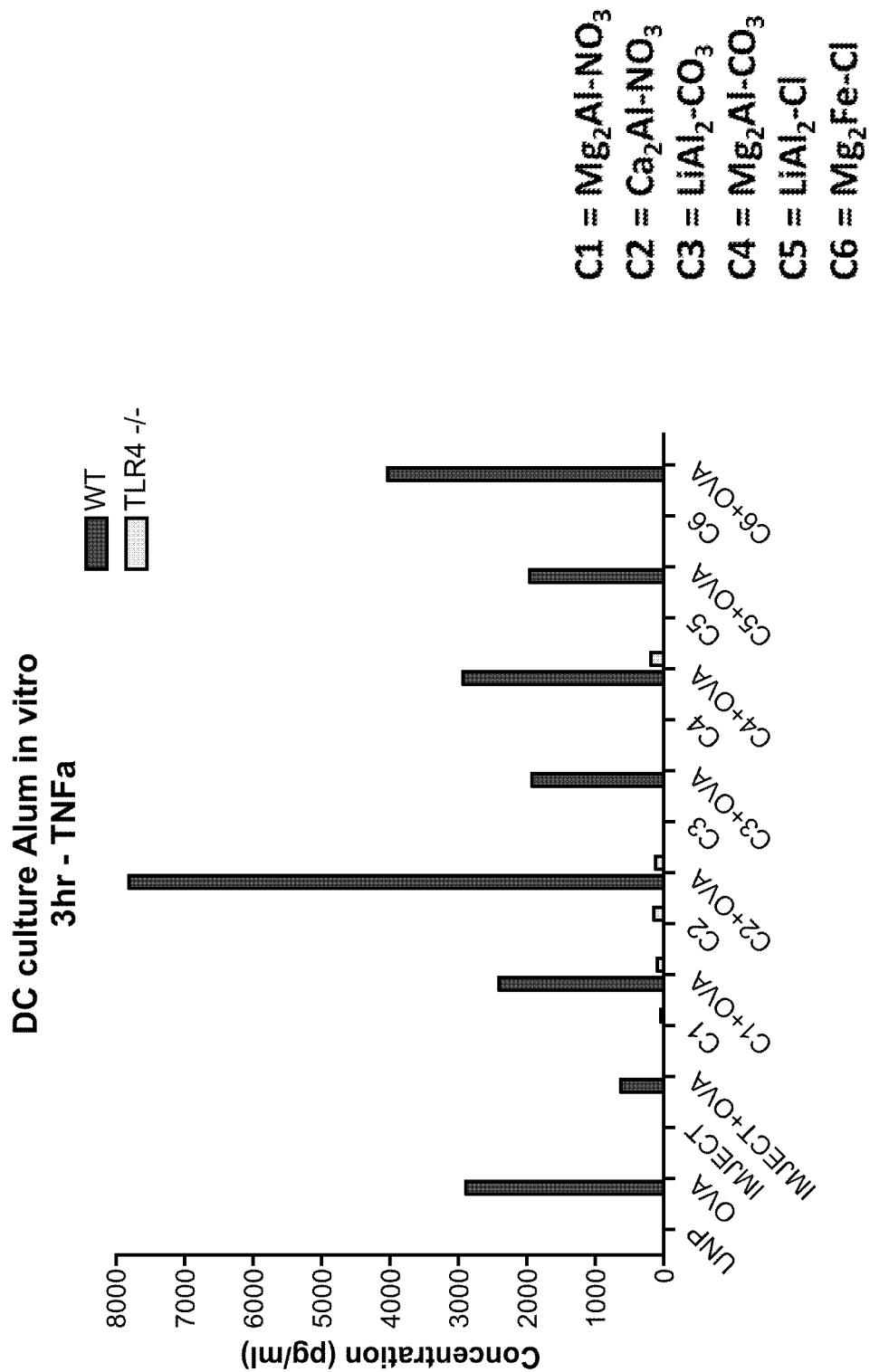
Figure 6C:
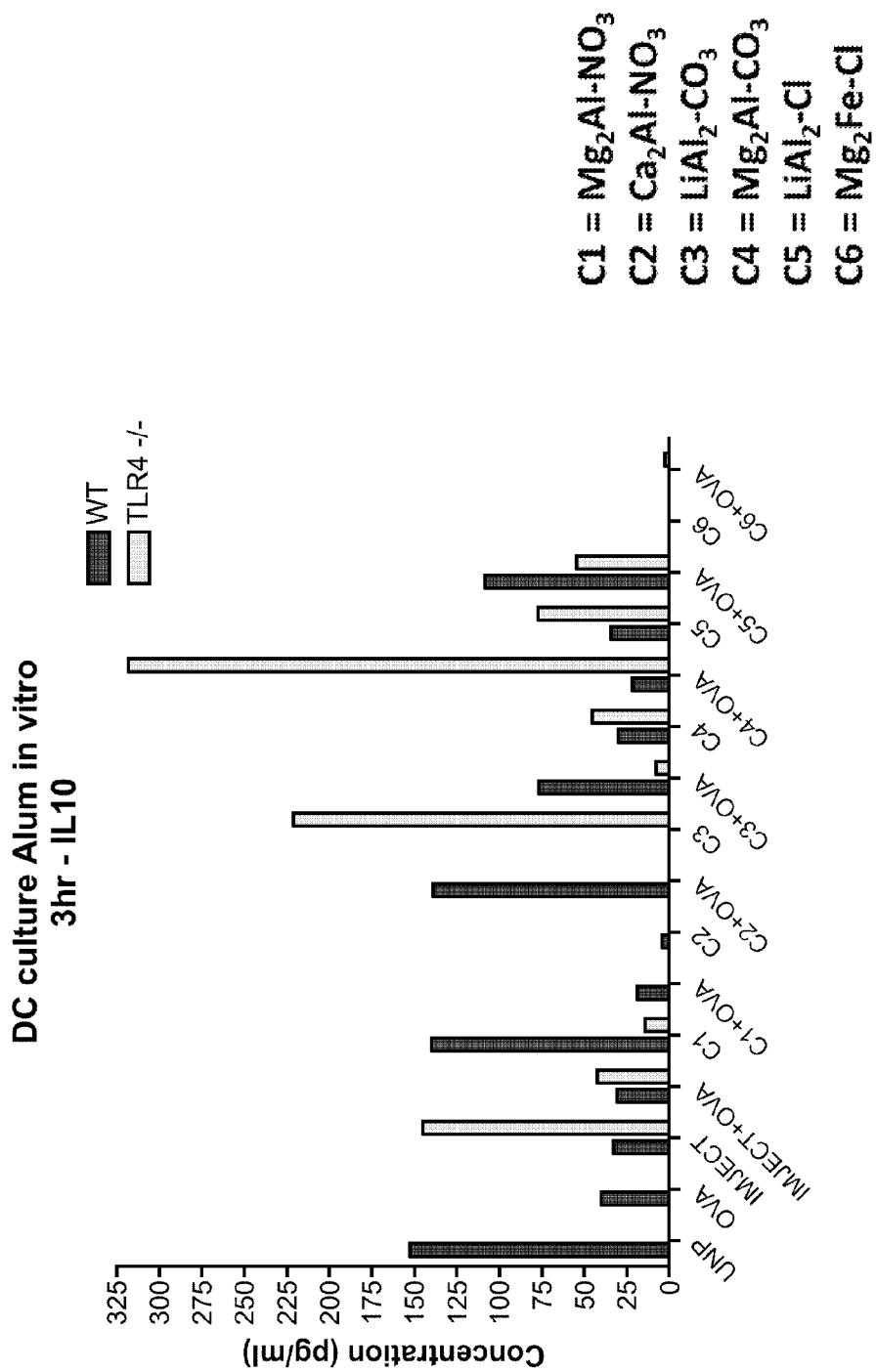

Some of the results are shown in FIG. 6.
FIG. 6a shows results for IL-1β (IL1b) after 3 hours.
FIG. 6b shows results for TNF-α, (TNFα) after 3 hours.
FIG. 6c shows results for after IL-10 (IL10) 3 hours.

3.5. Induction of Experimental Asthma to Assess In Vivo Response

Mice were sensitized by an intraperitoneal (i.p.) injections of 10 µg ovalbumin (OVA Worthington) adsorbed onto 1 mg Imject alum, alhydrogel or the LDH nanoparticles in 500 µl saline on days 0. On day 7 mice were boosted with 10 µg of OVA in 500 µl of saline. Ten days after the last injection, the mice were challenged by inhalation of OVA aerosols (grade III, 1% wt/vol in PBS (Sigma Aldrich)) generated by a jet nebulizer for 30 min. The aerosols were administered on day 17-18 and 19. On day 20 mice were sacrificed.

Mice were sacrificed by an overdose of 2.5% avertin, followed by bleeding.

3.5.1. OVA-Specific Antibody Levels

Serum samples were prepared from blood and OVA-specific antibody levels were measured.

Assays to measure OVA-specific IgE and IgG1 were undertaken using ELISA kits provided by BD Pharmingen, in accordance with the manufacturer's instructions. ELISA absorbent plates were procured from Greiner, and measurements recorded on a VIKTOR-3 96-well microplate photospectrometer instrument (PERKIN ELMER) at 450 nm.

Figure 7A:
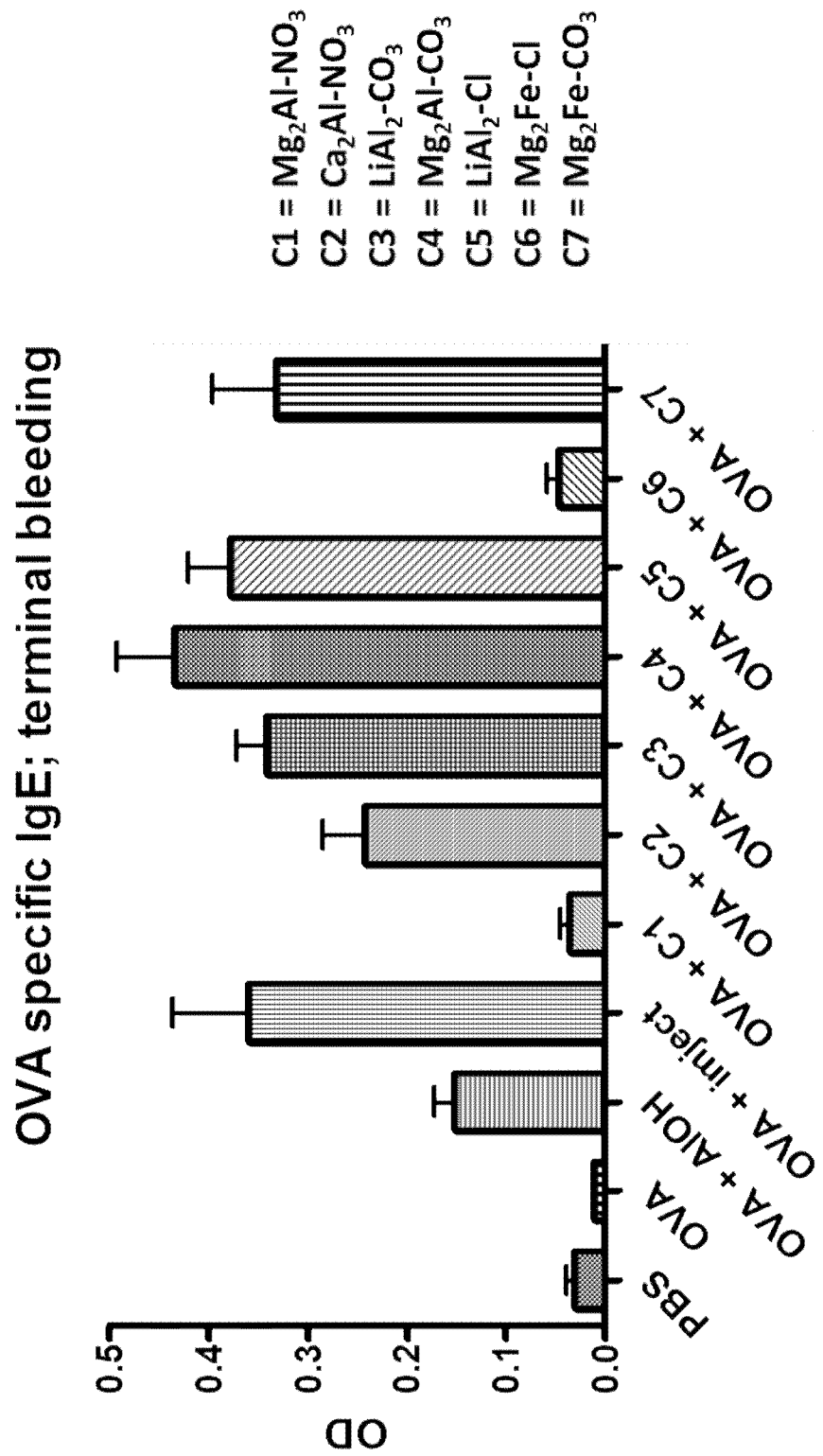
Figure 7B:
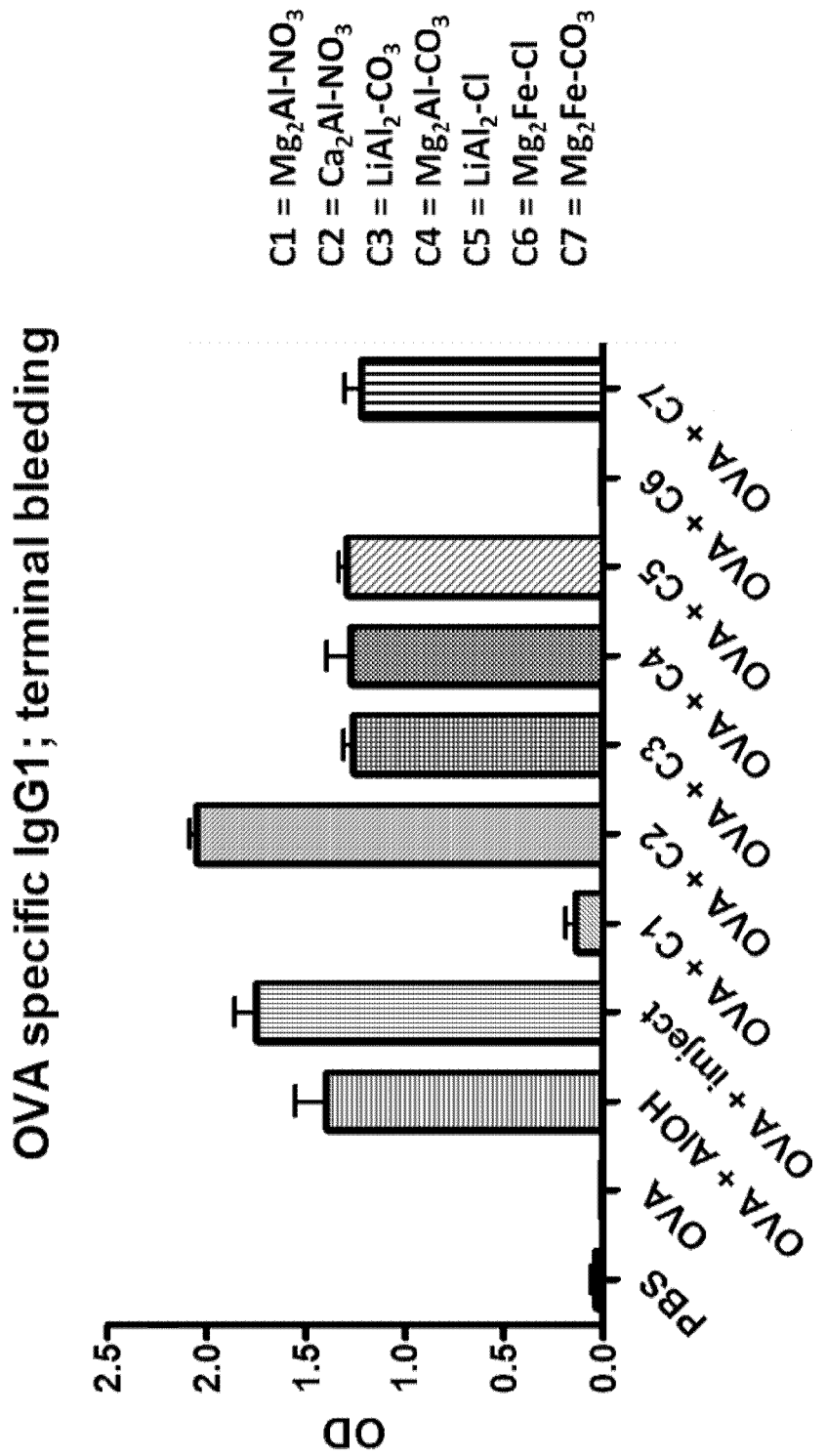

Some of the results are shown in FIG. 7
FIG. 7a shows the results for OVA-specific IgE
FIG. 7b shows the results for OVA-specific IgG1

3.5.2. Eosinophils in Broncho-Alveolar Lavage

Broncho-alveolar lavage (BAL) was performed by inserting a cannula in the trachea of the mouse. By lavage of 3×1 ml PBS containing 0.01 mM EDTA, cells were extracted from the lung alveolar space.

To quantify leukocytes in BAL the cells were stained with PE-labeled Siglec F (to label eosinophils), FITC-labeled MHCII, PE-Cy7 labeled GR1, PE-Cy5 labeled CD3/CD19 and APC-labeled CD11c (BD/eBioscience) and analysed by flow cytometry.

Figure 8:
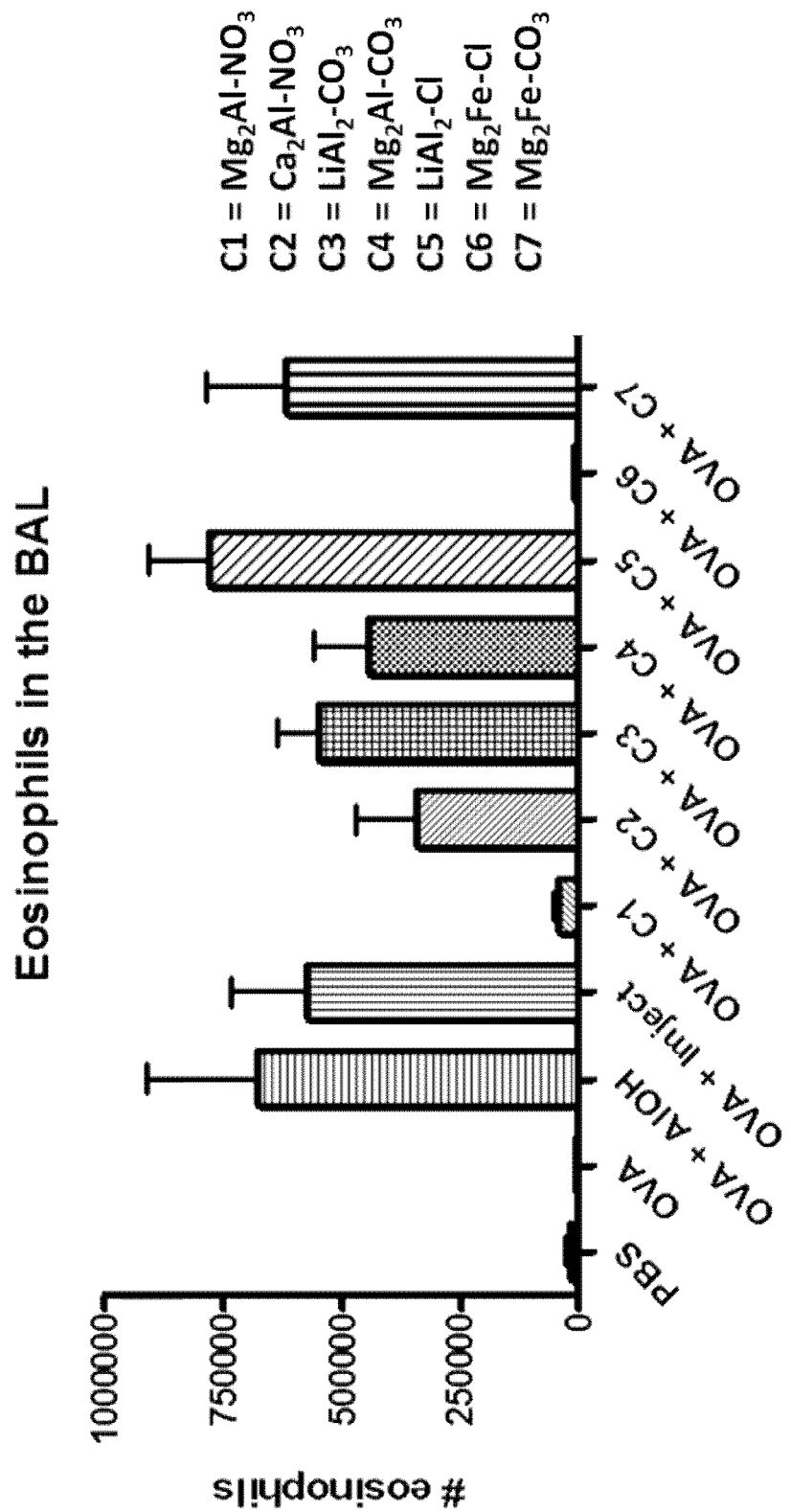

Some of the results are shown in FIG. 8.
Lungs were either inflated with PBS/OCT for histology or perfused with PBS through the pulmonary artery prior to mincing them to obtain a single cell suspension.

3.5.3. Cytokine Levels—$LiAl_2$—Cl, $LiAl_2$—$CO_3$, $Mg_2Al$—$NO_3$, $Mg_2Al$—$CO_3$, $Mg_2Fe$—Cl, $Ca_2Al$—$NO_3$ To determine the cytokine levels, MLN cells were plated in 96-wells round bottom plates at a density of $2*10^5$ cells per well and re-stimulated with 10 µg/ml OVA for 4 days. After 4 days, supernatants were harvested and stored at −20° C. until further examination. Using ELISA, the amount of IL-4, IL-5, IFNγ, IL10 (OptEIA—BD Bioscience), and IL-13 (R&D Systems) was measured in the supernatants.

Figure 9A:
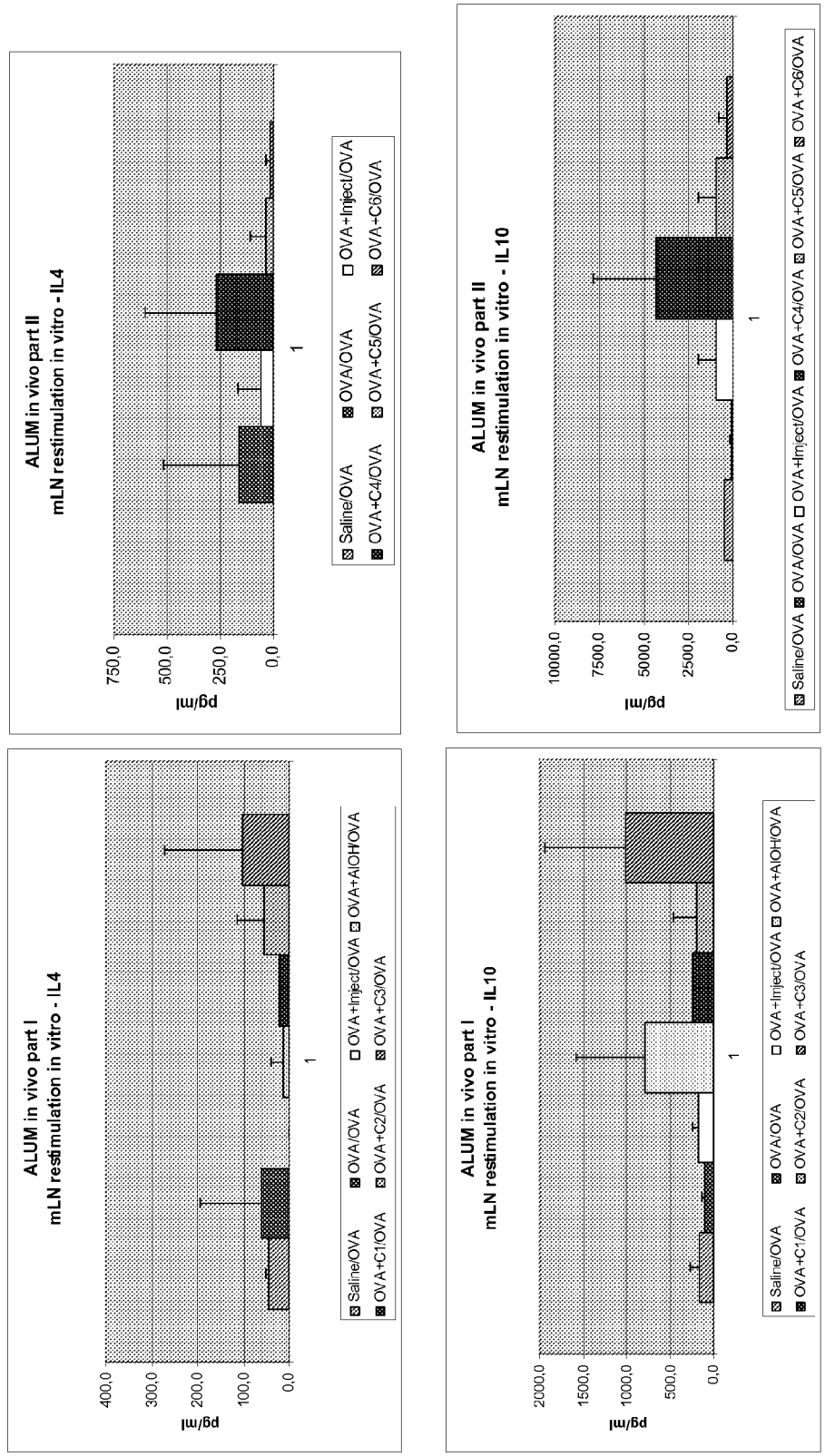
Figure 9B:
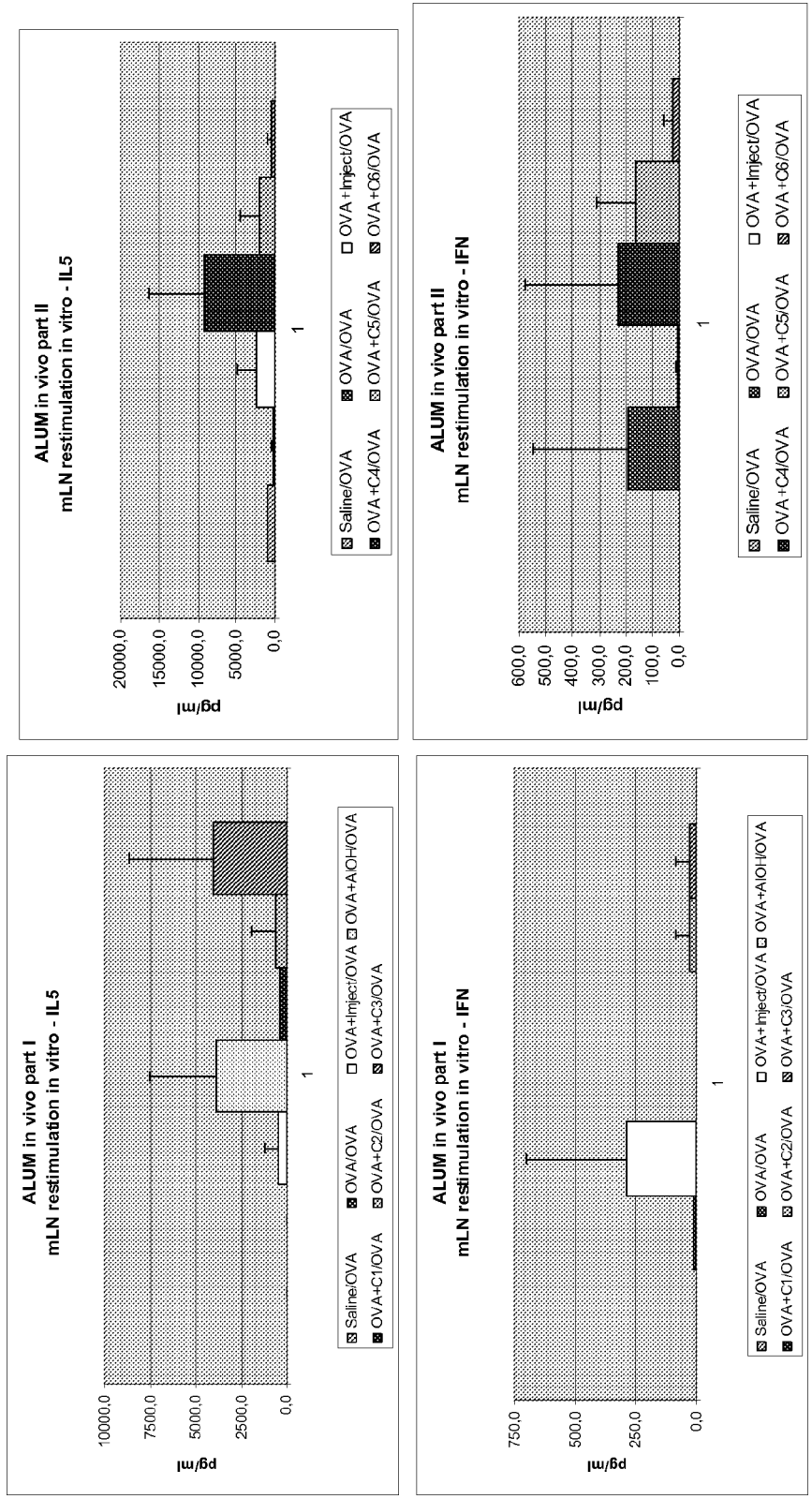
Figure 9C:
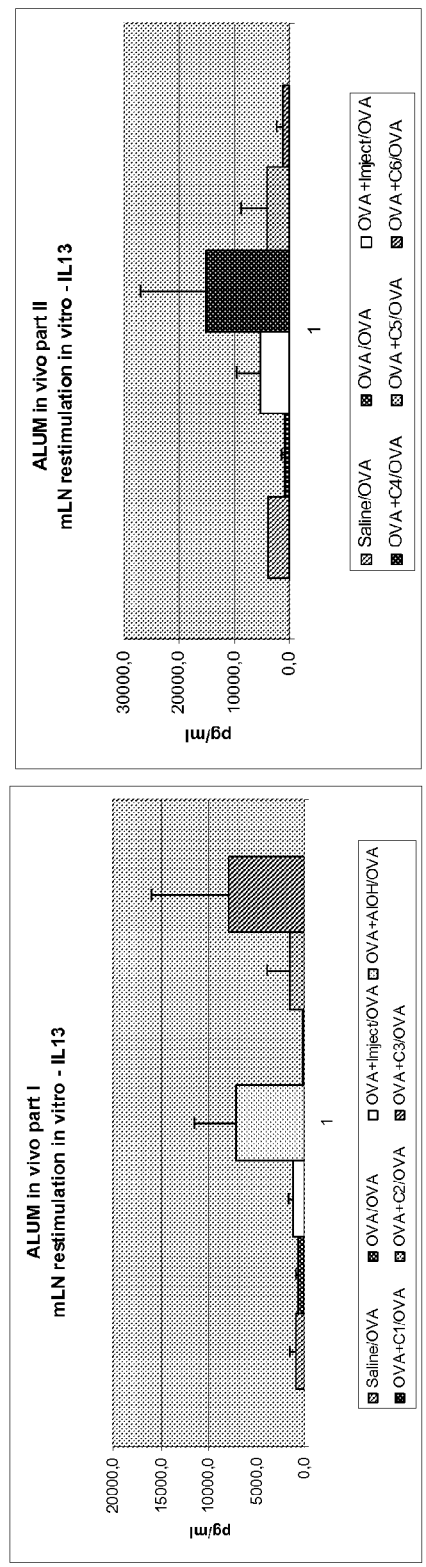
Figure 10A:
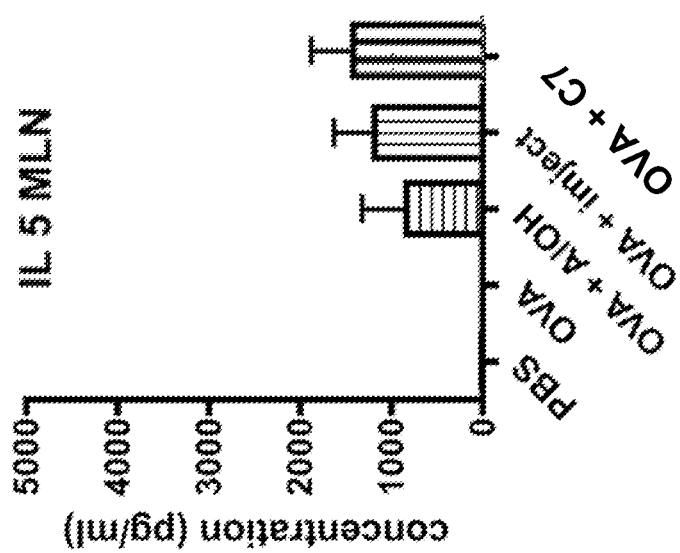
Figure 10B:
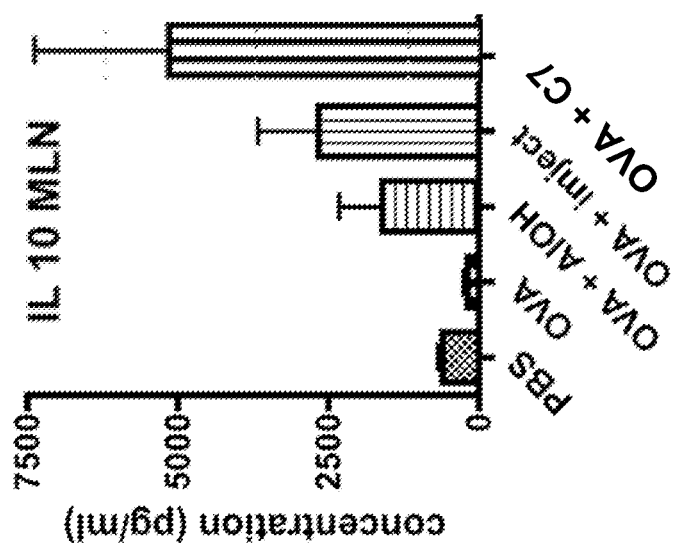
Figure 10C:
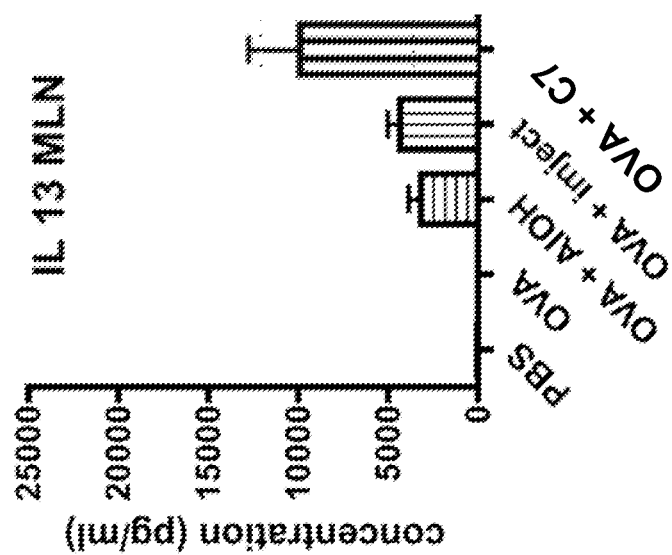
Figure 10D:
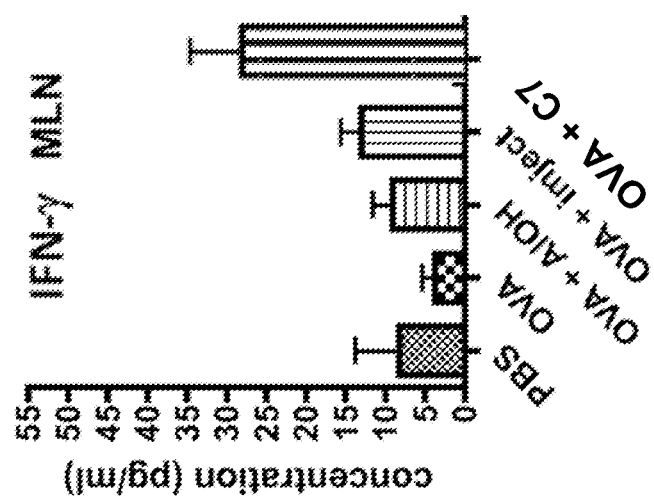

Results are shown in FIG. 9.
FIG. 9a shows the results for IL-4 and IL10
FIG. 9b shows the results for IL-5 and IFNγ
FIG. 9c shows the results for IL-13
The key shown in FIG. 9c applies for all of FIG. 9.

3.5.4. Cytokine Levels—$Mg_2Fe$—$CO_3$

To determine T cell subset polarisation after prime-boost and rechallenge as above, MLN cell suspensions were plated in 96-wells round bottom plates at a density of $2\times10^5$ cells per well and re-stimulated with 10 ng/ml OVA. After 4 days, supernatants were harvested and stored at −20° C. until further examination. Using ELISA, the amount of IL-5, IFN-γ, IL10 and IL-13 (eBioscience) was then measured in the supernatants.

Results are shown in FIG. 10.
FIG. 10a shows the results for IL-5
FIG. 10b shows the results for IL-10
FIG. 10c shows the results for IL-13
FIG. 10d shows the results for IFNγ

4. Summary of Results

4.1. Assessment In Vitro in Human DCs

Experiments in Section 2 were repeated multiple times with consistent results both for cytokine secretion and co-stimulatory molecule expression after exposure to compounds. Collectively, the data are summarised in Table 4.1. 'Rating' refers to the relative extent to which different compounds stimulate responses of human DC in vitro.

TABLE 4.1

| Human DC in vitro | |
| --- | --- |
| Compound | Rating |
| $LiAl_2$—Cl | + |
| $LiAl_2$—$CO_3$ | ++ |
| $Mg_2Al$—$NO_3$ | − |
| $Mg_2Al$—$CO_3$ | + |
| $Mg_2Fe$—Cl | − |
| $Ca_2Al$—$NO_3$ | ++ |

4.2. Assessment In Vitro in Mouse DCs and In Vivo in Mice

Experiments in section 3b were repeated twice, with multiple mice per group and at different time points in vivo, with consistent results. Collectively, the data are summarised in Table 4.2.

TABLE 4.2

Mouse DC in vitro and mice in vivo

| Compound | DC activation in vitro | T cell in vitro | T cell in vivo | Antibody induction in vivo | Eosinophils in BAL | Overall rating |
|---|---|---|---|---|---|---|
| LiAl$_2$—Cl | + | + | −/+ | − | ++ | + |
| LiAl$_2$—CO$_3$ | ++ | ++ | +++ | +++ | ++ | ++/+++ |
| Mg$_2$Al—NO$_3$ | − | ++ | − | − | − | −/+ |
| Mg$_2$Al—CO$_3$ | ++ | ++ | +++ | +++ | ++ | ++/+++ |
| Mg$_2$Fe—Cl | − | − | − | − | − | − |
| Mg$_2$Fe—CO$_3$ | *NT | NT | NT | +++ | ++ | ++/+++ |
| Ca$_2$Al—NO$_3$ | ++/+++ | +++ | ++ | +++ | ++ | ++/+++ |

*NT, not tested.
'DC activation in vitro' refers to the tests of sections 3.1 and 3.3.
'T cell in vivo', 'Antibody induction in vivo' and 'Eosinophils in BAL' refer to the tests of section 3.2
'T cell in vitro' refers to the tests of section 3.4.
'Overall rating' refers to the relative extent to which different compounds stimulate in vitro and in vivo responses in mice.

4.3. Overall Assessment

Data from all human and mouse experiments were combined to provide an overall assessment shown in Table 4.3. Note that Mg$_2$Fe—CO$_3$ was only studied in mice in vivo.

TABLE 4.3

Relative efficacy of different compounds

| Compound | Rating |
|---|---|
| LiAl$_2$—Cl | Average |
| LiAl$_2$—CO$_3$ | Good |
| Mg$_2$Al—NO$_3$ | Poor |
| Mg$_2$Al—CO$_3$ | Good |
| Mg$_2$Fe—Cl | Poor |
| Mg$_2$Fe—CO$_3$ | Good |
| Ca$_2$Al—NO$_3$ | Good |

5. Further Testing

5.1. Manufacture of LDHs

The following further LDH compounds were made:

Mg$_2$Al—Cl was prepared analogously to Mg$_2$Al—NO$_3$ (as described in section 1) except with Cl salts instead of nitrate salts.

Mg$_2$Fe—NO$_3$ was prepared analogously to Mg$_2$Fe—Cl (as described in section 1) except using nitrate salts in place of Cl salts.

LiAl$_2$—NO$_3$ was prepared in the same way as LiAl$_2$—Cl (as described in section 1) but with Li nitrate instead of Li chloride.

Ca$_2$Al—Cl was prepared in the same way as Ca$_2$Al—NO$_3$ (as described in section 1) but using chloride salts instead of nitrate salts.

Ca$_2$Al—CO$_3$ was prepared by heating Ca$_2$Al—Cl (as prepared above) at 400° C. for ca. 14 hours to dehydrate the LDH to form a layered double oxide (LDO). Then 0.12 g of the LDO was stirred with 0.11 g of Na$_2$CO$_3$ in 10 mL of deionised water at room temperature for 15 minutes. (NB. the compound was impure, and contained a significant amount of a CaCO$_3$ impurity.)

5.2. Elemental Microanalysis of LDHs

C, H, and N were analysed. The samples were quantitatively digested through oxidative combustion to determine the content of each element. The results, together with formulae calculated from them, are set out below.

TABLE 5.1

Elemental analysis of further LDHs

| Compound | Formula | C % Calcd | C % Obsd | H % Calcd | H % Obsd | N % Calcd | N % Obsd |
|---|---|---|---|---|---|---|---|
| Mg$_2$Fe—NO$_3$ | Mg$_2$Fe(OH)$_6$](NO$_3$)•H$_2$O | 0 | 0 | 2.82 | 2.78 | 4.90 | 4.78 |
| Mg$_2$Al—Cl | Mg$_2$Al(OH)$_6$]Cl•H$_2$O | 0 | 0 | 3.49 | 3.48 | 0 | 0 |
| Ca$_2$Al—CO$_3$ | Not determined due to impurity | | | | | | |
| LiAl$_2$—NO$_3$ | Li$_{0.95}$Al$_2$(OH)$_6$](NO$_3$)0.95•(H$_2$O)$_{3.5}$ | 0 | 0 | 4.60 | 4.13 | 4.67 | 4.23 |
| Ca$_2$Al—Cl | [Ca$_2$Al(OH)$_6$]Cl•(H$_2$O)$_3$ | 0 | 0 | 4.06 | 4.21 | 0 | 0 |

5.3. Particle Size Distribution

For three of the new LDHs, X-ray diffraction data was used in combination with the particle size data collected for analogous materials to estimate particle size (via the Scherrer equation).

Mg$_2$Fe—NO$_3$: 100 nm
Mg$_2$Al—Cl: 185 nm
Ca$_2$Al—CO$_3$: 373 nm

This was not possible for the LiAl$_2$—NO$_3$ and Ca$_2$Al—Cl materials, but a comparison of the powder diffraction data by eye with that of the LiAl$_2$—Cl and Ca$_2$Al—NO$_3$ materials suggests that LiAl$_2$—NO$_3$ should have particle size broadly similar to the LiAl$_2$—Cl (see section 1.3, above) and Ca$_2$Al—Cl should be about the same as Ca$_2$Al—NO$_3$ (see section 1.3, above).

5.4 Physicochemical Properties

Surface pKa values of compounds were obtained from published references.

TABLE 5.2

Physicochemical properties of further LDH compounds

|  | $Mg_2Al$—Cl | $Ca_2Al$—$CO_3$ | $LiAl_2$—$NO_3$ | $Ca_2Al$—Cl |
|---|---|---|---|---|
| Surface pKa | <5.2 | 12-13.71 | <5.2 | 12-13.71 |

5.5. In Vitro Testing on Human Dendritic Cells

Testing of these further LDH compounds is being carried out using the same methodology as the earlier tests described in section 2, except that a Guava EasyCyte Flow Cytometer is being used for the flow cytometery experiments (with data analysed in FlowJo), and a BMG LabTech FLUOstar Omega plate reader is being used for ELISA.

Initial results indicate that the $Ca_2Al$—Cl and $Ca_2Al$—$CO_3$ are also LDH compounds that appear to be having an activation effect on the human dendritic cells.

The invention claimed is:

1. A composition comprising
   (i) a long range ordered, layered double hydroxide (LDH) of a formula:

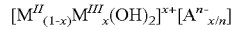

in which
   $M^{II}$ is a divalent metal cation or a mixture of two or more divalent metal cations,
   $M^{III}$ is a trivalent metal cation or a mixture of two or more trivalent metal cations, or a mixture of one or more trivalent metal cation with one or more quadravalent metal cation,
   x is such that the ratio of $M^{II}$ to $M^{III}$ is 2:1 or 1:4 and
   A is an interlayer anion having a charge n, wherein A is selected from conjugate bases of acids having a pKa of 1 or higher, with the proviso that when $M^{II}$ comprises $Ca^{+2}$, A is selected from conjugate bases of acids having a pKa of −4 or higher;
   and
   (ii) one or more antigens;
   wherein the long range ordered, layered double hydroxide compound is not a LDH-hybrid where the anion A has been replaced by a biologically active agent and/or the one or more antigens and/or other antigens.

2. The composition of claim 1, further comprising dendritic cells in combination therewith.

3. The composition of claim 2, further comprising T cells in combination with the treated dendritic product.

4. The composition of claim 1, wherein the layered double hydroxide compound comprises:
   long-range cation-ordering; and
   a surface pKa that is greater than 5.2.

5. The composition layered double hydroxide compound of claim 1, wherein the layered double hydroxide compound is a Mg—Al based compound of the formula with x=⅓ and A is $CO_3^{2-}$, or $HCO_3^-$.

6. The composition of claim 1, wherein the layered double hydroxide compound is a Mg—Al based compound of the formula with x=⅓ and A is $CO_3^{2-}$ HO—, $HOO^-$, $ClO^-$, or $HCO_3^-$.

7. The composition of claim 1, wherein the one or more antigens is selected from: virally-derived antigens; bacterially-derived antigens; fungal-derived antigens, yeast- and mould-derived antigens; protozoa-parasite derived antigens; metazoa-parasite derived antigens; tumour antigens; blood group antigens; antigens from allergens and immunosensitivities; antigens from transplantation; self antigens; and DNA vaccination antigens.

8. The composition of claim 1, wherein the layered double hydroxide compound is present as a particle having a particle diameter from 200 nm to 750 nm.

9. A composition comprising
   (i) a long range ordered, layered double hydroxide (LDH) of a formula

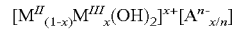

in which $M^{II}$ is Mg, $M^{III}$ is Al, x=⅓, such that the ratio of $M^{II}$ to $M^{III}$ is 2:1, and A is $CO_3^{2-}$ and
   (ii) one or more antigens selected from: virally-derived antigens; bacterially-derived antigens; fungal-derived antigens; yeast- and mould-derived antigens; protozoa-parasite derived antigens; metazoa-parasite derived antigens; tumour antigens; blood group antigens; antigens from allergens and immunosensitivities; antigens from transplantation; self antigens; and DNA vaccination antigens.

* * * * *